(12) United States Patent
Sabesan et al.

(10) Patent No.: US 9,241,673 B2
(45) Date of Patent: Jan. 26, 2016

(54) SYSTEMS AND METHODS FOR VALIDATING MONITORING DEVICE PLACEMENT AND LOCATIONS

(71) Applicant: CYBERONICS, INC., Houston, TX (US)

(72) Inventors: Shivkumar Sabesan, Houston, TX (US); Gerrard M. Carlson, Houston, TX (US)

(73) Assignee: CYBERONICS, INC., Houston, TX (US)

( * ) Notice: Subject to any disclaimer, the term of this patent is extended or adjusted under 35 U.S.C. 154(b) by 120 days.

(21) Appl. No.: 14/042,430

(22) Filed: Sep. 30, 2013

(65) Prior Publication Data

US 2015/0094605 A1 Apr. 2, 2015

(51) Int. Cl.
| | |
|---|---|
| *A61B 5/02* | (2006.01) |
| *A61B 5/00* | (2006.01) |
| *A61B 5/0245* | (2006.01) |
| *A61B 5/0402* | (2006.01) |
| *A61B 7/04* | (2006.01) |
| *A61B 5/024* | (2006.01) |
| *A61B 5/0424* | (2006.01) |

(52) U.S. Cl.
CPC ............. *A61B 5/7221* (2013.01); *A61B 5/0245* (2013.01); *A61B 5/0402* (2013.01); *A61B 5/684* (2013.01); *A61B 7/045* (2013.01); *A61B 5/02438* (2013.01); *A61B 5/0424* (2013.01)

(58) Field of Classification Search
CPC ................................ A61B 5/024; A61B 5/025
See application file for complete search history.

(56) References Cited

U.S. PATENT DOCUMENTS

| | | |
|---|---|---|
| 6,708,063 B2 | 3/2004 | Czgan et al. |
| 2004/0039420 A1 | 2/2004 | Jayne et al. |
| 2005/0137490 A1 | 6/2005 | Scheiner et al. |
| 2007/0208390 A1* | 9/2007 | Von Arx ............. A61N 1/36514 607/32 |
| 2008/0243196 A1* | 10/2008 | Libbus ................. A61N 1/0551 607/2 |
| 2009/0012415 A1 | 1/2009 | Thiagarajan et al. |
| 2010/0057157 A1 | 3/2010 | Govari et al. |
| 2012/0095521 A1 | 4/2012 | Hintz |
| 2012/0172684 A1 | 7/2012 | Buchheim et al. |
| 2012/0271372 A1* | 10/2012 | Osorio ............................ 607/17 |
| 2012/0283809 A1 | 11/2012 | Cholette et al. |
| 2013/0131465 A1 | 5/2013 | Yamamoto et al. |

OTHER PUBLICATIONS

Phan, D. H. et al., "Estimation of Respiratory Waveform and Heart Rate Using an Accelerometer," 30th Annual International IEEE EMBS Conference, Vancouver, British Columbia, Canada, Aug. 20-24, 2008, pp. 4916-4919.

(Continued)

*Primary Examiner* — Theodore Stigell
*Assistant Examiner* — Natasha Patel

(57) ABSTRACT

This disclosure relates to devices, systems, and methods for validating locational data for a monitoring device. The external monitoring device located on a patient may include one or more processors, one or more memory devices, one or more power devices, one or more heart rate detection devices, and one or more heart sound detection devices. Further, the method may include determining a plurality of status of an external monitoring device located on a patient via one or more processors based on obtained heart rate data and obtained heart sound data. The external monitoring device state may be generated via a validation module based on the heart rate data and the heart sound data.

23 Claims, 13 Drawing Sheets

(56) References Cited

OTHER PUBLICATIONS

International Application No. PCT/US2014/056373,Search Report and Written Opinion dated Mar. 31, 2015, 17 pages.
Adjei,P., R. Surges,et al. (2009). "Do subclinical electrographic seizure patterns affect heart rate and its variability?" Epilepsy Res87(2-3): 281-5.
Blumhardt, L. D., P. E. Smith, et al. (1986). "Electrocardiographic accompaniments of temporal lobe epileptic seizures." Lancetl(8489): 1051-6.
Britton,J. W.,G. R. Ghearing,et al. (2006). "The ictal bradycardia syndrome: localization and lateralization." Epilepsia47(4): 737-44.
Digennaro, G., P. P. Quarato,et al. (2004). "Ictal heart rate increase precedes EEG discharge in drug-resistant mesial temporal lobe seizures." Clin Neurophysiol115(5):1169-77.
Epstein,M.A.,M. R. Sperling,et al. (1992). "Cardiac rhythm during temporal lobe seizures." Neurology42(1): 50-3.
Galimberti, C. A., E. Marchioni, et al. (1996). "Partial epileptic seizures of different origin variably affect cardiac rhythm." Epilepsia37(8): 742-7.
Garcia, M.,C. D'Giano, et al. (2001). "Ictal tachycardia: its discriminating potential between temporal and extratemporal seizure foci." Seizure10(6): 415-9.
Jeppesen,J.,Beniczky S,et al. (2010). "Detection of epileptic-seizures by means of power spectrum analysis of heart rate variability: A pilot study." Technology and Health Care18: 417-426.
Keilson, M. J., W. A. Hauser,et al. (1989). "Electrocardiographic changes during electrographic seizures." Arch Neurol46(11):1169-70.
Kerem,D. H. and A. B. Geva (2005). "Forecasting epilepsy from the heart rate signal." Med Bioi Eng Comput43(2):230-9.
Leutmezer,F., C. Schernthaner, et al. (2003). "Electrocardiographic changes at the onset of epileptic seizures." Epilepsia44(3): 348-54.
Li, I. M.,J. Roche,et al. (1995). "Ictal ECG changes in temporal lobe epilepsy." Arq Neuropsiquiatr53(3-B): 619-24.
Marshall, D.W., B. F. Westmoreland,et al. (1983). "Ictal tachycardia during temporal lobe seizures." Mayo Clin Proc58(7): 443-6.
Massetani, R.,G. Strata,et al. (1997). "Alteration of cardiac function in patients with temporal lobe epilepsy: different roles of EEG-ECG monitoring and spectral analysis of RR variability." Epilepsia38(3): 363-9.
Mayer, H., F. Benninger, et al. (2004). "EKG abnormalities in children and adolescents with symptomatic temporal lobe epilepsy." Neurology63(2): 324-8.
Nei, M.,R. T. Ho, et al. (2000). "EKG abnormalities during partial seizures in refractory epilepsy." Epilepsia4l(5): 542-8.
Nilsen, K. B.,M. Haram,et al. (2010). "Is elevated pre-ictal heart rate associated with secondary generalization in partial epilepsy?" Seizure19(5): 291-5.
Novak, V., A. L. Reeves,et al. (1999). "Time-frequency mapping of R-R interval during complex partial seizures of temporal lobe origin." J Auton Nerv Syst77(2-3):195-202.
Oliveira, G. R., A. Gondim Fde, et al. (2007). "Heart rate analysis differentiates dialeptic complex partial temporal lobe seizures from auras and non•epileptic seizures." Arq Neuropsiquiatr65(3A): 565-8.
Opherk, C., J. Coromilas, et al. (2002). "Heart rate and EKG changes in 102 seizures:analysis of influencing factors." Epilepsy Res52(2):117-27.
O'Regan, M. E. and J. K. Brown (2005). Abnormalities in cardiac and respiratory function observed during seizures in childhood. 11 Dev Med ChildNeurol47(1): 4-9.
Rugg-Gunn, F. J., R. J. Simister,et al. (2004). "Cardiac arrhythmias in focal epilepsy:a prospective long-term study." lancet364(9452): 2212-9.
Schernthaner,C., G. Lindinger,et al. (1999). 11 Autonomic epilepsy—the influence of epileptic discharges on heart rate and rhythm. Wien KlinWochenschr111(10): 392-401.
Smith, P. E.,S. J. Howell, et al. (1989). "Profiles of instant heart rate during partial seizures." Electroencephalogr Clin Neurophysiol72(3): 207-17.
Toth, V., L. Hejjel, et al. (2010). "Periictal heart rate variability analysis suggests long-term postictal autonomic disturbance in epilepsy." Eur J Neurol17(6): 780-7.
Van Elmpt, W. J., T. M. Nijsen,et al. (2006). "A model of heart rate changes to detect seizures in severe epilepsy." Seizure15(6): 366-75.
Vaughn, B. V., S. R. Quint, et al. (1996). "Monitoring Heart Period Variability Changes During Seizures II. Diversity and Trends." J. Epilepsy9:27-34.
Weil, S., S. Arnold,et al. (2005). "Heart rate increase in otherwise subclinicalseizures is different in temporal versus extratemporal seizure onset: support for temporal lobe autonomic influence." Epileptic Disord7(3):199-204.
Wilder-Smith, E. and S. H. Lim (2001). "Heart rate changes during partial seizures: a study amongst Singaporean patients." BMC Neuroll:5.
Zijlmans, M., D. Flanagan,et al. (2002). "Heart rate changes and ECG abnormalities during epileptic seizures: prevalence and definition of an objective clinical sign." Epilepsia43(8): 847-54.

\* cited by examiner

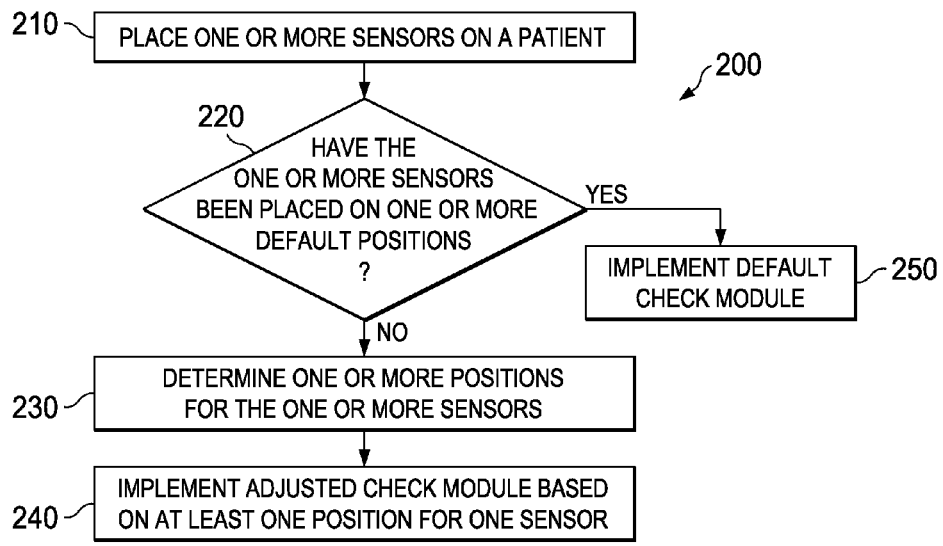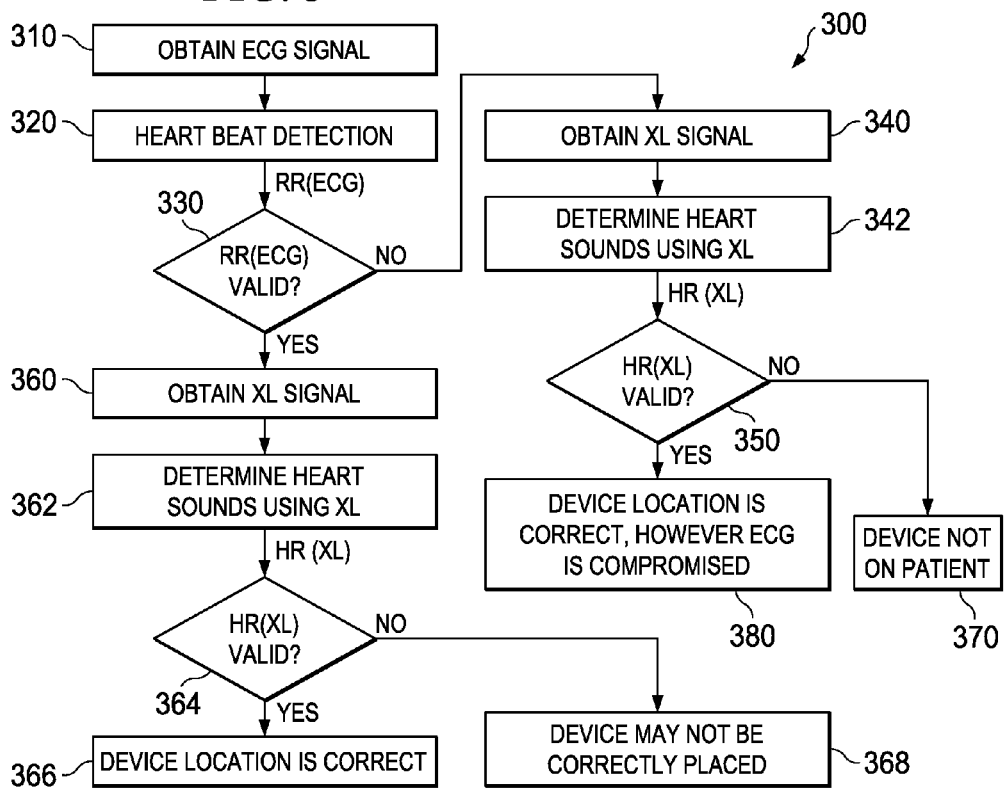

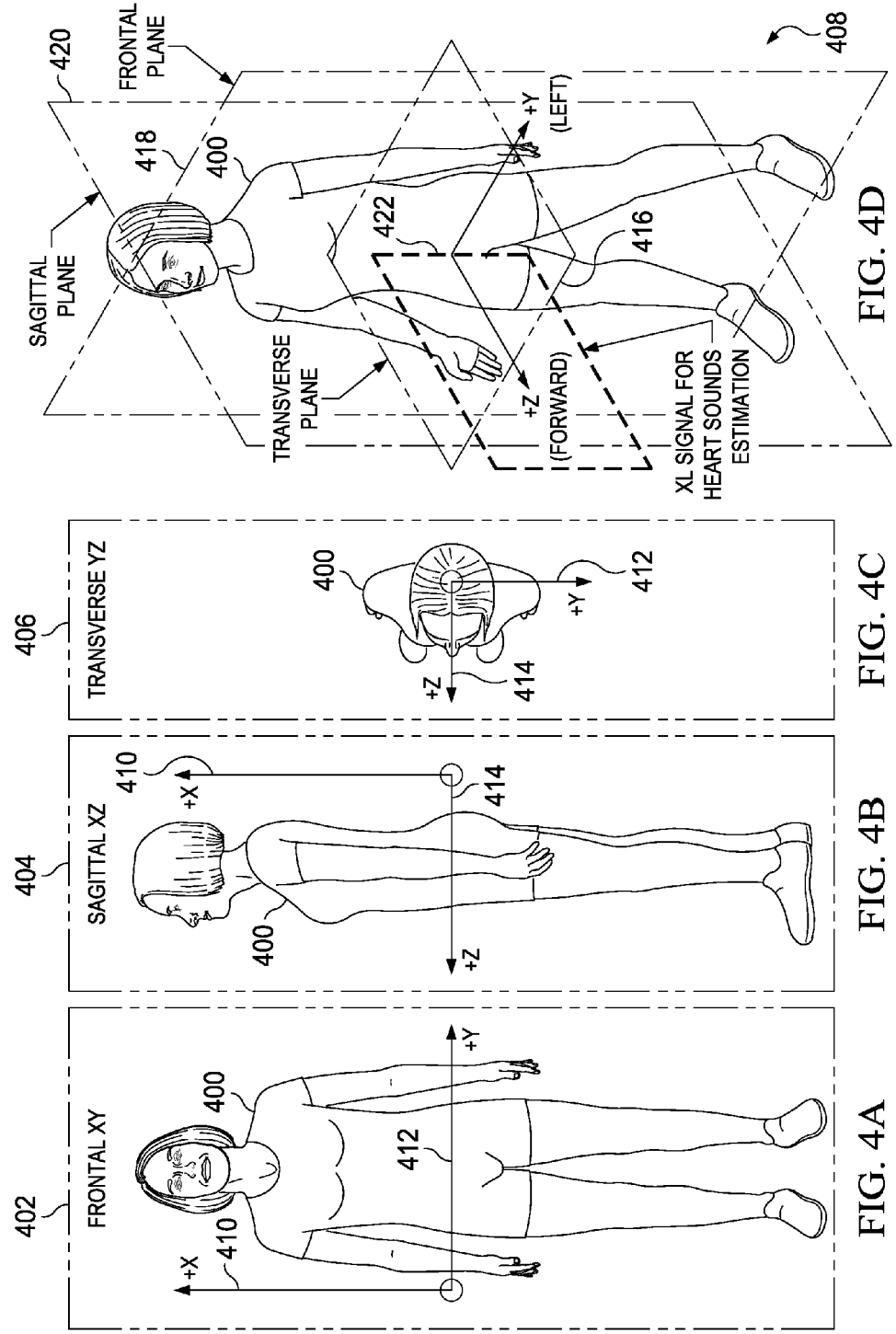

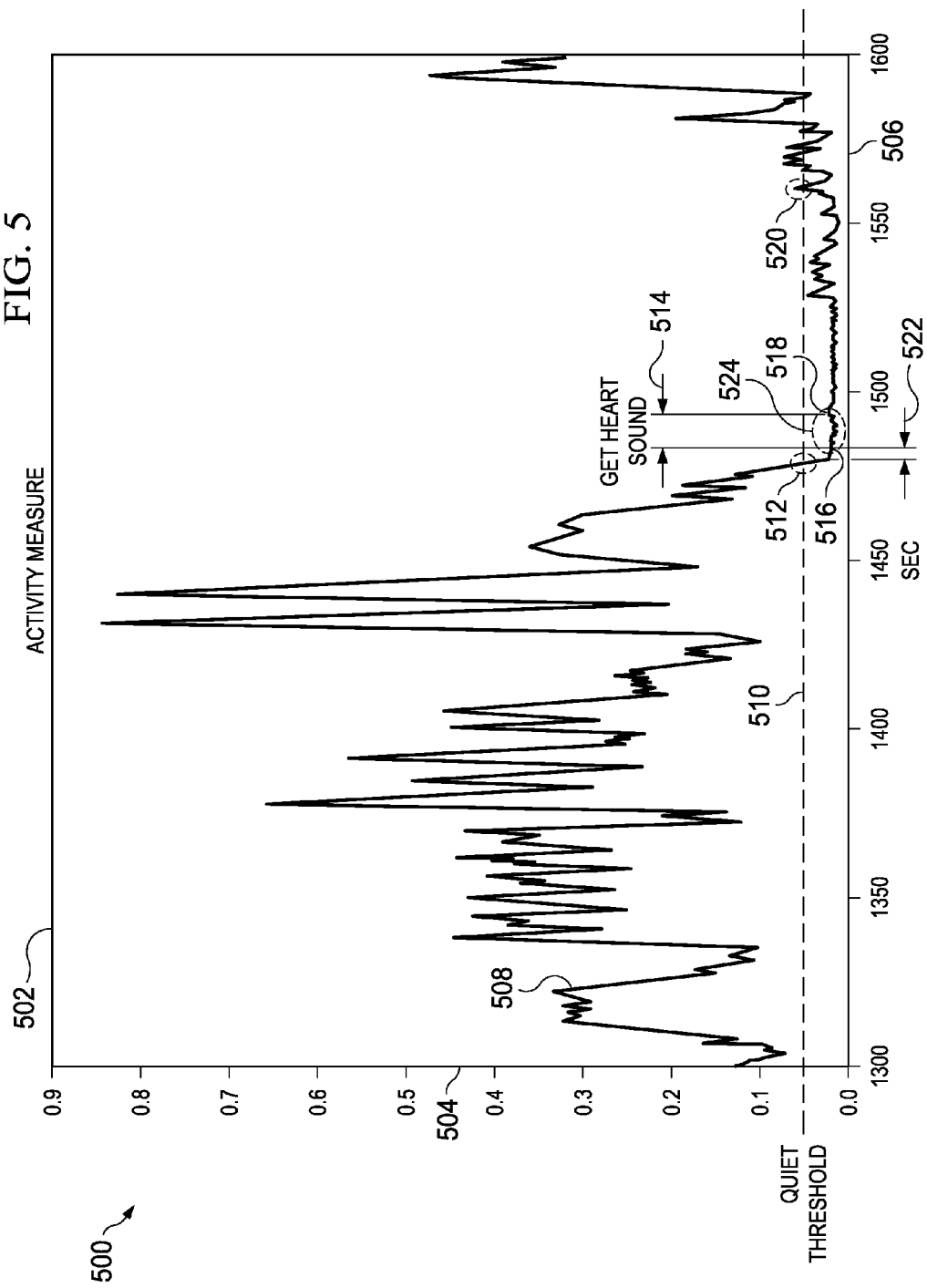

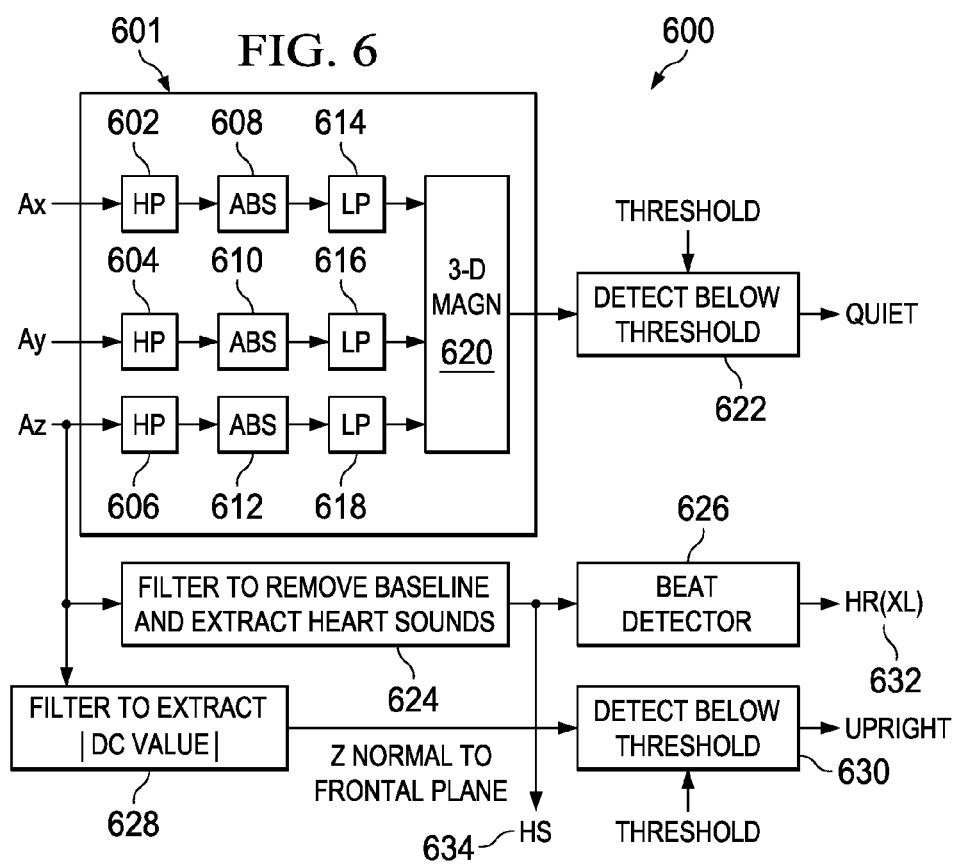

| 802 | 804 | 806 |
|---|---|---|
| HR (ECG) | HR (XL) | MONITORING DEVICE STATUS |
| X | X | DEVICE IS NOT PLACED ON THE PATIENT |
| O | X | DEVICE LOCATION IS ON THE PATIENT, HOWEVER MAY NOT BE IN CORRECT LOCATION AND/OR LOCATION RANGE |
| X | O | DEVICE LOCATION IS CORRECT; THE PATCH OR THE ECG SIGNAL INTEGRITY IS COMPROMISED |
| O | O | DEVICE LOCATION IS CORRECT |

810, 812, 814, 816

808 — X = NOT DETECT
O = DETECT

FIG. 8B
800B

| HR (ECG) | HR (XL) | DECISION |
|---|---|---|
| X (810) | X | IMD IS NOT SENSING AND THE DEVICE LOCATION/ORIENTATION HAS CHANGED. THIS MAY BE DUE TO EITHER LEAD BREAKAGE, HEADER MISALIGNMENT OR PATIENT PULLING OR TWIDDLING WITH THE DEVICE RESULTING IN DEVICE LOCATION CHANGE AND STRAIN ON THE CUFF ELECTRODES |
| O (812) | X | IMD IS SENSING, HOWEVER, THE DEVICE LOCATION AND/OR ORIENTATION HAS CHANGED (MAY HAVE IMPLICATIONS ON ANTENNA TUNING FOR RELAY) |
| X (814) | O | THE IMD LOCATION HAS NOT SHIFTED (IMD LOCATION MAY SHIFT DUE TO THE PATIENT TWIDDLING THE DEVICE) BUT THE DEVICE IS NOT SENSING RELIABLY SUGGESTING EITHER TOO MUCH MUSCLE NOISE (DUE TO NECK AND ARM MOVEMENTS) OR THE LEADS ARE COMPROMISED |
| O (816) | O | IMD IS SENSING RELIABLY |

808: X = NOT DETECT
O = DETECT

SYSTEMS AND METHODS FOR VALIDATING MONITORING DEVICE PLACEMENT AND LOCATIONS

FIELD OF THE DISCLOSURE

The present disclosure is generally related to systems and methods for validating monitoring device locations.

SUMMARY

In a particular embodiment, an external monitoring device located on a patient may include one or more processors, one or more memory devices, one or more power devices, one or more heart rate detection devices, and one or more heart sound detection devices.

In a particular embodiment, a method may include obtaining via one or more processors heart rate data, obtaining heart sound data, and/or determining via the one or more processors an external monitoring device state where the determined external monitoring device state is produced via a validation module. The validation module utilizes the obtained heart rate data and the obtained heart sound data to generate one or more determined external monitoring device states.

In a particular embodiment, a system may include an external monitoring device located on a patient, a base station, and/or an external computing device. The external monitoring device may include one or more processors, one or more memory devices, one or more power devices, one or more heart rate detection devices, and one or more heart sound detection devices. The base station may include a base station processor, a base station memory, and a base station power supply. The external device may include an external device processor, an external device memory, and an external device power supply.

The features, functions, and advantages that have been described can be achieved independently in various embodiments or may be combined in yet other embodiments, further details of which are disclosed with reference to the following description and drawings.

BRIEF DESCRIPTION OF THE DRAWINGS

FIG. 2 is a flow chart for validating the location of an external monitoring device, according to one embodiment;

FIG. 3 is another flow chart for validating the location of an external monitoring device, according to one embodiment;

FIGS. 4A-4D are illustrations of a plurality of planes relating to an individual, according to various embodiments;

FIG. 5 is an illustration, which can be utilized to determine a quiet period, according to one embodiment;

FIG. 6 is a block diagram of the system and/or the device for validating one or more locations for an external monitoring device, according to one embodiment;

FIG. 8A is a table illustrating various conditions based on data obtained from an electrocardiography signal and a heart sound signal, according to one embodiment;

FIG. 8B is another table illustrating various conditions based on data obtained from an electrocardiography signal and a heart sound signal, according to one embodiment;

DETAILED DESCRIPTION

Figure 1A:
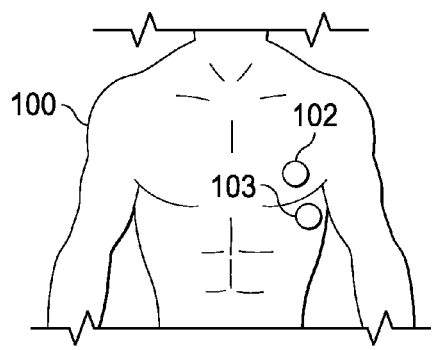
FIGS. 1A-1F are diagrams illustrating various locations for an external monitoring device, according to various embodiments.

In various embodiments, determining a device's (e.g., monitoring device, detection device, therapy device, communication device, etc.) location on a patient's body may be critical to delivering reliable performance from the device (e.g., monitoring device, detection device, therapy device, communication device, etc.) and/or any other related device. For example, a heart sound detection device's location and/or a heartbeat detection device's location may be important for generating accurate heart beat measurements, accurate heart sound measurements, and/or to ensure patient compliance with respect to device wearability guidelines. In one situation, where the electrocardiography ("ECG") signal is either weak or absent, determining the device's (e.g., heart beat detection device, heart sound detection device, etc.) location may assist in troubleshooting whether the signal is weak due to incorrect device placement or due to a dysfunctional electrode and/or electrode patch (and/or a lead in an implantable medical device). In another situation, where the ECG signal is noisy, determining the device's location in combination with the signal integrity check module may assist in the troubleshooting process because the signal may be noisy due to the device's location or due to a dysfunctional electrode and/or electrode patch (and/or a lead in an implantable medical device). In another situation, where the ECG signal is noisy from a source (e.g., implantable medical device, etc.), the system, device, and/or method may determine heart beats simultaneously from another source, such as heart sounds, which may help troubleshoot whether the noise is due to lead breakage, header misalignment, and/or movement/misalignment of the one or more devices (e.g., a patient twiddling the device and/or causing communication error due to antenna mismatch).

For example, one or more processors may determine a device's (e.g., heart beat detection device, heart sound detection device, etc.) location on a patient and based at least in part on this information, generate a first error message. The first error message may be that the external monitoring device is in a location that is incorrect and/or outside of a tolerance range. The first error message may be generated, transmitted, compiled, and/or stored. In another example, the one or more processors may determine a device's location on a patient and based at least in part on this information, generate a second error message. The second error message may be that the external monitoring device is in a location that is correct and/or inside a tolerance range but that a problem has occurred with the electrode and/or electrode patch (and/or a lead in an implantable medical device). In another example, the one or more processors may determine a device's location on a patient and based at least in part on this information, generate a third error message. The third error message may be that the external monitoring device is in a location that is correct and/or inside a tolerance range. In addition, the electrode and/or electrode patch (and/or a lead in an implantable medical device) is working properly but the ECG signal is weak and/or absent. In another example, the one or more processors may determine a device's location on a patient and based at least in part on this information, generate a fourth error message. The fourth error message may be that the external monitoring device is in a location that is correct and/or inside a tolerance range. In addition, the electrode and/or electrode patch (and/or a lead in an implantable medical device) and the ECG signal are working properly. However, there is a problem (e.g., lack of communication, power off, error with one or more components, etc.) with one or more of the other devices (e.g., implantable medical device, base station, mobile device, server, computer, etc.).

In FIG. 1A, a diagram illustrating a body 100 of a patient with a monitoring device 102 is shown, according to one embodiment. Monitoring device 102 may be placed on various parts of body 100. In various examples, monitoring device 102 may be placed on any external part of body 100. In one example, monitoring device 102 may be positioned at the upper left thorax of the patient. In one example, the upper left thorax of the patient may be an optimal position for the place of monitoring device 102. In another example, monitoring device 102 may be located on the back of body 100 at a location that mirrors the upper left thorax of the patient. In another example, monitoring device 102 may be located at a position below the upper left thorax 103. In this example, position below the upper left thorax 103 is a pre-cordial location. This pre-cordial location may be utilized with second condition 812 of FIG. 8. In one example utilizing this pre-cordial location, the device may obtain acceptable ECG signals but not accelerometer ("XL") based heart sound signals. In this example, the device location is on the patient, however, the device may not be on or close to the upper left thorax.

In various examples, alternative heart beat detection sensors may be utilized in place of the XL sensor. In one example, an optical sensor (e.g., infrared LED/Photo diode, etc.) may be utilized to validate heart beat detection. For heart rate estimation, one or more acoustic sensors may be utilized as a complement to the XL sensor with the appropriate signal preconditioning and/or as standalone functionality. In another example, heart rate estimation can be implemented via one or more microphones where the one or more microphones are designed to pick up one or more heart sounds. In this example, the art of phonocardiography may use one or more sensitive microphones to pick up one or more heart sounds. In this example, the postural information may not be available from an acoustic sensor. However, beat-to-beat rate information may be derived from the one or more acoustic sensors. In this example, activity may have less influence on microphone-based measurements and therefore the rate may be captured even with some patient movement. In this example, the patient's speech may need to be appropriately separated from the acoustic signal data, which makes rate estimation viable with some normal daily activity. In this example, the patient's vocal data would need to be determined and speech data would need to be removed from the acoustic signal data (e.g., signal preconditioning). In another example, the sensors may be packaged in multiple separate packages (e.g., the ECG device may be worn on the chest as a patch and the XL package may be worn on a strap about the chest) that are in communication with each other or with a separate base station that then compiles and/or processes the two different signals.

In another example, this disclosure may be utilized to determine whether the heart rate determined by the implantable device is reliable. Further, a determination of whether the device orientation/location on the chest has changed which may cause a loss of communication between one or more devices (e.g., IMD, IPG, etc.) and one or more communication interfaces. In one example, this may be used to provide feedback to the antenna tuning circuit to adjust the signal strength by adjusting the antenna orientation on one or more device (e.g., mobile device, tablet, etc.).

Figure 1B:
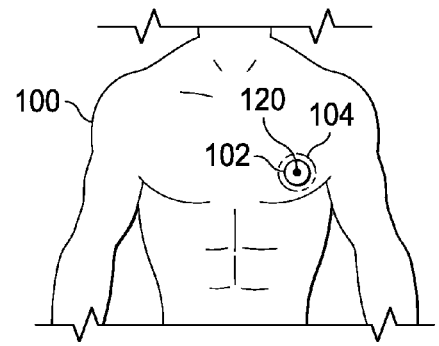
Figure 1C:
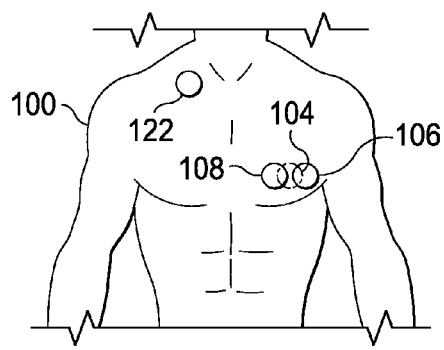

In another example, monitoring device 102 may be positioned at the upper left thorax of the patient where monitoring device 102 may function properly as long as monitoring device 102 is within a tolerance area 104 (see FIG. 1B). Tolerance area 104 may be an area (e.g., 1%, 2%, 3%, 5%, 7.5%, 10%, 50%, 100%, 200%, etc.) larger than the area occupied by monitoring device 102. Tolerance area 104 may be an area surrounding an anchoring position 120. Anchoring position 120 may be the center position for an optimal placement of monitoring device 102 (see FIG. 1B). In another example shown in FIG. 1C, monitoring device 102 may operate inefficiently, inaccurately, and/or may not operate at all when monitoring device 102 is positioned outside of tolerance area 104, which is indicated by a first misaligned position 106, a second misaligned position 108, and/or an Nth misaligned position 122.

In one example, tolerance area 104 may be an area 15% bigger than monitoring device 102. Tolerance area 104 may be based on anchoring position 120. Therefore, if monitoring device 102 is positioned where any part of monitoring device 102 is outside of tolerance area 104, monitoring device 102 may fail to operate. However, in another example, if monitoring device 102 is positioned where any part of monitoring device 102 is outside of tolerance area 104, then the effectiveness of monitoring device 102 may be reduce. For example, 1% of the area of monitoring device 102 being outside of tolerance area 104 may reduce the efficiency of monitoring device 102 by 5%. In another example, 5% of the area of monitoring device 102 being outside of tolerance area 104 may reduce the efficiency of monitoring device 102 by 15%. Whereas, 10% of the area of monitoring device 102 being outside of tolerance area 104 may reduce the efficiency of monitoring device 102 by 50%. It should be noted that any percentage may occur and/or be utilized in these examples.

Figure 10:
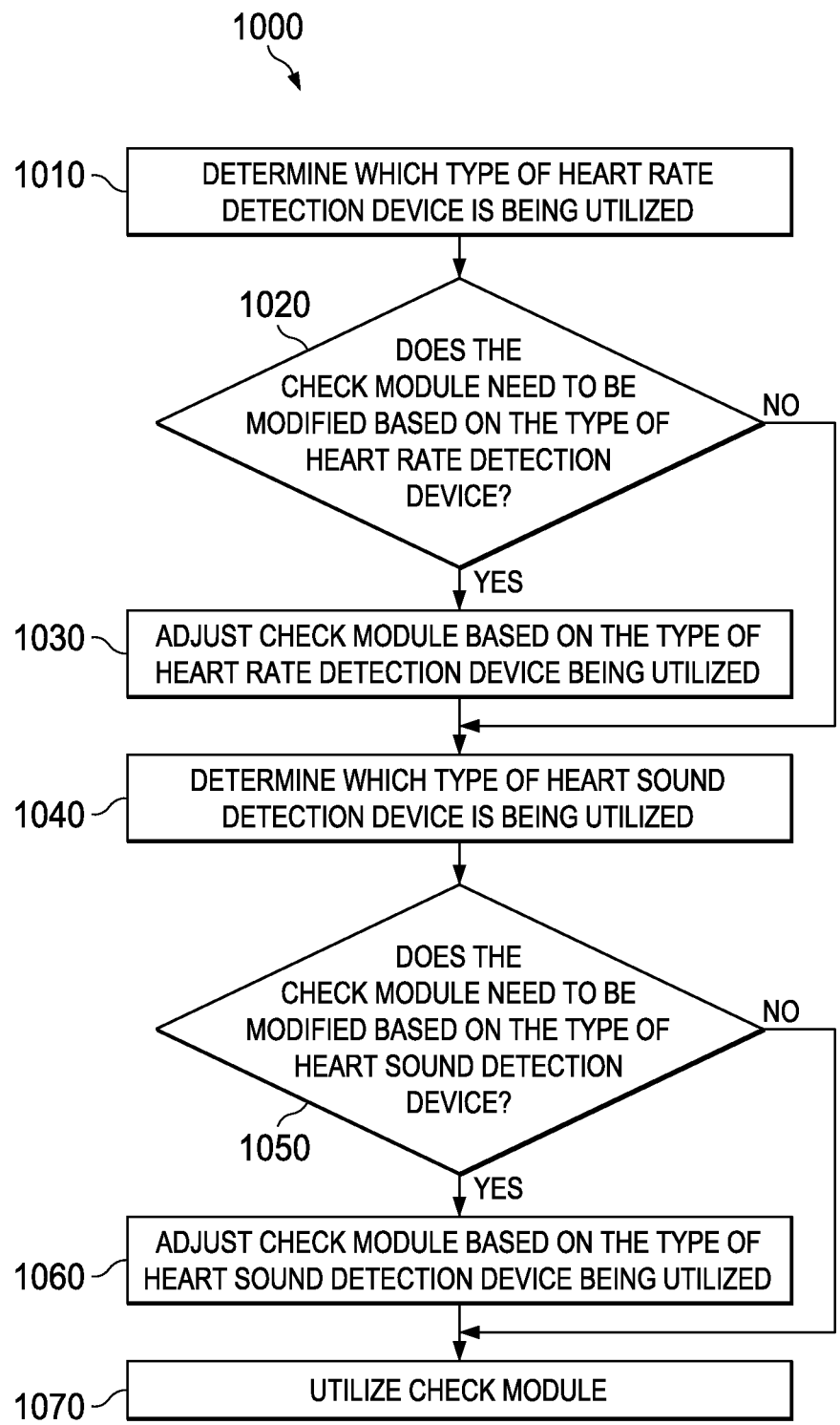
FIG. 10 is a flow chart for validating the location of one or more external devices, according to one embodiment.

In another example, one or more processors may determine the location and area occupied by monitoring device 102. In this example, the one or more processors may compare the location and area occupied by monitoring device 102 to one or more reference data points to determine whether monitoring device 102 is in the proper location and area. If monitoring device 102 is in the proper location and occupies the correct area, a message may be generated and/or transmitted which indicates that monitoring device 102 is in the proper location and area. Once monitoring device 102 is known to be in the correct position and/or area, then various procedures may be utilized (FIGS. 3, 8, 10, etc.). If monitoring device 102 is not in the proper location and/or occupying the correct area, one or more messages may be generated and/or transmitted. For example, a message to move monitoring device 102 a specific distance (e.g., 1 inch, 2 inches, etc.) in a specific direction (e.g., up, down, left, right, up diagonal and to the left, down diagonal and to the right, etc.) may be generated and/or transmitted. Further, this procedure may continue in a feedback loop until monitoring device 102 is in the correct location.

Figure 1D:
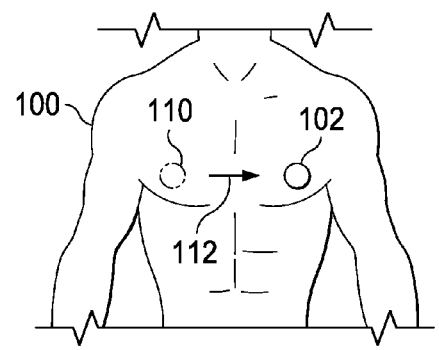

In another example, monitoring device 102 may be positioned at a first location 110 (e.g., outside of tolerance area 104) where a default verification procedure may not work effectively. In one example, a first algorithm 112 may be utilized to modify the default verification procedure to compensate for monitoring device 102 being located at first location 110. These modifications may virtual move monitoring device 102 from first location 110 to a location within tolerance area 104 (see FIG. 1D). For example, when monitoring device 102 is positioned at first location 110, first algorithm 112 may modify the heart sound data to compensate for monitoring device 102 being located at first location 110. In addition, first algorithm 112 may modify the heart rate data to compensate for monitoring device 102 being located in first location 110. Further, first algorithm 112 may modify the default algorithm to compensate for monitoring device 102 being located at first location 110. First algorithm 112 may modify any data, algorithm, program, device, and/or any other element of the monitoring system to compensate for monitoring device 102 being located at first location 110.

Figure 1E:
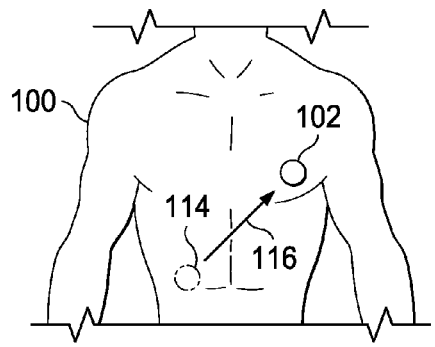
Figure 1F:
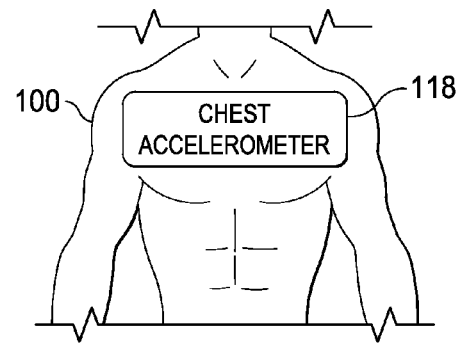

In FIG. 1E, monitoring device 102 is in a second location 114 (e.g., outside of tolerance area 104) where a default verification procedure may not work effectively. In one example, a second algorithm 116 may be utilized to modify the default verification procedure to compensate for monitoring device 102 being located at second location 114. These modifications may virtual move monitoring device 102 from second location 114 to a location within tolerance area 104. For example, if monitoring device is positioned where any part of monitoring device 102 is outside of tolerance area 104, then the effectiveness of monitoring device 102 may be reduce (see FIG. 1C). For example, 1% of the area of monitoring device 102 being outside of tolerance area 104 may reduce the efficiency of monitoring device 102 by 5%. However, second algorithm 116 may modify any data, algorithm, program, device, and/or any other element of the monitoring system to compensate for monitoring device 102 being located 1% outside of tolerance area 104 to eliminate and/or reduce the 5% reduction in efficiency. In this example, the reduced efficiency may be eliminated (e.g., 0%) and/or reduced (e.g., 1%, 2%, 3%, 4%, 4.1%, etc.). In another example, shown in FIG. 1F, monitoring device 102 may include a chest accelerometer 118.

In FIG. 2, a flow chart for validating the location of an external medical device 200 is shown, according to one embodiment. In one example, external medical device 200 is monitoring device 102. The method may include placing one or more sensors on a patient (step 210). The method may include one or more processors determining whether the one or more sensors have been placed in one or more default positions (step 220). If the one or more sensors have been placed in the one or more default positions, then the method may include implementing the default check module (step 250). If the one or more sensors have not been placed on the one or more default positions, then the method may determine one or more positions for the one or more sensors (step 230). The method may include implementing an adjusted check module based on at least one position for one of the one or more sensors (step 240).

If monitoring device 102 is in the proper location and occupies the correct area, a message may be generated and/or transmitted which indicates that monitoring device 102 is in the proper location and area. Once monitoring device 102 is known to be in the correct position and/or area, then various procedures may be utilized (FIGS. 3, 8, 10, etc.). If monitoring device 102 is not in the proper location and/or occupying the correct area, one or more messages may be generated and/or transmitted. For example, a message to move monitoring device 102 a specific distance (e.g., 1 inch, 2 inches, etc.) in a specific direction (e.g., up, down, left, right, up diagonal and left, down diagonal and right, etc.) may be generated and/or transmitted. Further, this procedure may continue in a feedback loop until monitoring device 102 is in the correct location.

In one example, a modification algorithm (e.g. first algorithm 112, second algorithm 116, Nth algorithm, etc.) may be utilized to modify the default verification procedure to compensate for monitoring device 102 being located at a non-default location (e.g., outside of tolerance area 104). These modifications may virtual move monitoring device 102 from a non-default location to a location within tolerance area 104. Modification algorithm may modify any data, algorithm, program, device, and/or any other element of the monitoring system to compensate for monitoring device 102 being located at a non-default location.

"Cardiac cycle" refers to one complete PQRSTU interval of the patient's heart functioning, ending with the P wave of the next succeeding cardiac cycle. "Interbeat interval" refers to the time period between a predetermined point in a first cardiac cycle of the patient and the same predetermined point in the immediately succeeding cardiac cycle of the patient, for example an R-R interval, a P-P interval, or a T-T interval. Interbeat intervals may comprise a single interval or a moving average (either simple or weighted) of several consecutive intervals. "Cardiac period" is a length of time between a first point in the cardiac cycle of the patient and a second, later point. Exemplary points include a P-wave, a Q-wave, an R-wave, an S-wave, a T-wave, and a U-wave of the cardiac cycle, which can be readily identified by electrocardiography ("EKG") or other techniques of monitoring the electrical activity of the heart.

In FIG. 3, another flow chart for validating the location of an external medical device 300 is shown, according to one embodiment. In one example, external medical device 300 is monitoring device 102. The method may include obtaining one or more electrocardiography ("ECG") signals (step 310). The method may include determining and/or detecting one or more heart beat characteristics (step 320). The method may include that one or more processors determines whether one or more heart beat characteristics (e.g., R-R interval, P-P interval, T-T interval, P wave, PR segment interval, PQ segment interval, QRS interval, ST segment interval, etc.) are valid (e.g., RR(ECG)) (step 330). If the one or more heart beat characteristics are valid, then the method may include obtaining one or more XL signals (step 360). The method may include determining one or more heart sound characteristics (and/or heart sound signals) via an accelerometer (and/or any other heart sound detecting device) (step 362). The method may include that one or more processors determine whether the one or more heart sound characteristics are valid (e.g., HR(XL)) (step 364). If the one or more heart sound characteristics are valid (e.g., HR(XL)), then the method may determine that the device's location is correct (step 366). If the one or more heart sound characteristics are invalid (e.g., HR(XL)), then the method may determine that the device may not be correctly placed (step 368). If the one or more heart beat characteristics determined at step 330 are invalid, then the method may determine one or more heart sound characteristics (and/or heart sound signals) via an accelerometer (and/or any other heart sound detecting device) (step 340). The method may include via one or more processors determining one or more heart sounds (and/or heart characteristics) utilizing one or more XL signals (step 342). The method may include that one or more processors determine whether the one or more heart sound characteristics are valid (e.g., HR(XL)) (step 350). If the one or more heart sound characteristics are invalid, then the method may determine that the device's location is incorrect (e.g., device is not on patient) (step 370). In another example, the device's location may need to be on the upper left thorax of the patient. If the device is not located on the upper left thorax of the patient, then the device may be in an incorrect location. If the one or more heart sound characteristics are valid, then the method may determine that the device's location is correct but that the ECG signal quality is compromised (step 380). The validation of the heart beat characteristics and the heart sound characteristics may occur in series and/or in parallel.

For example, one or more processors may determine a device's (e.g., heart beat detection device, heart sound detection device, etc.) location on a patient and based at least in part on this information, generate a first error message. The first error message may be that the external monitoring device is in a location that is incorrect and/or outside of a tolerance range. In another example, one or more processors may determine a device's location on a patient and based at least in part on this information, generate a second error message. The second error message may be that the external monitoring device is in a location that is correct and/or inside a tolerance range but that a problem has occurred with the electrode and/or electrode patch (and/or a lead in an implantable medical device). In another example, one or more processors may determine a device's location on a patient and based at least in part on this information, generate a third error message. The third error message may be that the external monitoring device is in a location that is correct and/or inside a tolerance range. In addition, the electrode and/or electrode patch (and/or a lead in an implantable medical device) is working properly but the ECG signal is weak and/or absent. In another example, one or more processors may determine a device's location on a patient and based at least in part on this information, generate a fourth error message. The fourth error message may be that the external monitoring device is in a location that is correct and/or inside a tolerance range. In addition, the electrode and/or electrode patch (and/or a lead in an implantable medical device) and the ECG signal are working properly. However, there is a problem (e.g., lack of communication, power off, error with one or more components, etc.) with the one or more devices (e.g., implantable medical device, base station, mobile device, server, computer, etc.).

In FIGS. 4A-4D, illustrations of a plurality of planes relating to an individual are shown, according to various embodiments. In FIG. 4A, a first image 402 illustrates an X-Axis 410 and a Y-Axis 412 superimposed onto a person 400. In this example, data from the frontal XY plane may be obtained via one or more sensing devices. In FIG. 4B, a second image 404 illustrates X-Axis 410 and a Z-Axis 414 superimposed onto person 400. In this example, data from the sagittal XZ plane may be obtained via one or more sensing devices. In FIG. 4C, a third image 406 illustrates Y-Axis 412 and Z-Axis 414 superimposed onto person 400. In this example, data from the transverse YZ plane may be obtained via one or more sensing devices. In FIG. 4D, a fourth image 408 illustrates the combination of a transverse plane 416, a frontal plane 418, and a sagittal plane 420 superimposed on person 400. In one example, one or more frontal Z data readings 422 may be utilized to estimate one or more heart sounds. In one example, one or more data signals from an accelerometer may be utilized as one or more frontal Z data readings 422.

In various examples, a patient position (e.g., standing up, laying down facing up, laying down facing down, sitting down, etc.) may be determined by utilizing one or more data points from the above-referenced planes. For example, utilizing an $A_z$ data point filtered to extract the DC value may allow for a person's physical position to be determined (see FIG. 6). In one example, if the $A_z$ data point has a DC value of 0, then the patient is standing up. In another example, if the $A_z$ data point has a DC value of −1, then the patient is laying down facing up. Further, if the $A_z$ data point has a DC value of 1, then the patient is laying down facing down. This information may be utilized to determine whether the patient is in the right position to allow for the determination of one or more baseline values (e.g., quiet threshold, heart sound baseline data, heart rate baseline data, blood pressure, etc.). If the patient is not in the right position, then the device and/or system may request that the patient move to the right position. For example, an audio and/or visual command may request that the patient move to the correct position. In an example, a message may state, "Please move to a standing up position and remain still." In another example, a visual message may read, "Please lay down on the floor looking upward." In another example, the system and/or device may modify one or more algorithms, data, and/or devices to compensate for the patient being in a different position then a default position (e.g., the position that the algorithms, data, and/or devices utilize as a base position).

In one embodiment, the sagittal plane includes accelerometer sensitive axes (e.g., one or more frontal Z data readings 422, etc.). These axes may include one along the vertical direction and one along the anteroposterior direction. In one example, a patient's breathing may cause the periodic movement of the thorax, which changes the incline of the accelerometer, which may be utilized to determine data relating to heart rate and/or heart sound.

In FIG. 5, an illustration for determining a quiet period 500 is shown, according to one embodiment. In this example, one or more baseline heart sound readings are being obtained. In one example, an activity measurement graph 502 may include a Sound-Axis 504 (Y-Axis) and a Time-Axis 506 (X-Axis). Activity measurement graph 502 may also include a heart sound line 508 and a quiet threshold 510. Heart sound line 508 may include a plurality of data points relating to a patient's heart sound level over a time period. Quiet threshold 510 may be a data point and/or data range where the patient's heart sound level may be utilized to generate a baseline heart sound level 524. In one example, the patient's heart sound level enters (and/or is below) quiet threshold 510. In one example, the generation of baseline heart sound level 524 may start as soon as the patient's heart sound level enters into quiet threshold 510. In another example, a buffer time period 522 may be utilized to ensure that the patient's heart sound level has remained in and/or under quiet threshold 510 for a specific time period before baseline heart sound level 524 starts to be generated. In one example, once the patient's heart sound level has remained in and/or under quiet threshold 510 for buffer time period 522, then baseline heart sound level 524 may be generated. In an example, baseline heart sound level 524 may need to be produced for a first time period 514 to be valid. First time period 514 may include a start time 516 and an end time 518. In another example, baseline heart sound level 524 may need to be produced for a second time period to be valid. In various examples, the time period for validation of baseline heart sound level 524 may vary based on the characteristics (e.g., height, weight, age, health, ailments, etc.) of the patient and/or the physical position (e.g., standing up, laying down facing up, laying down facing down, sitting down, patient moving slightly, patient having average movement, patient having above-average movement, etc.) of the patient. In another example, heart sound line 508 may exit and/or rise above quiet threshold 510 at one or more exit points 520. In one example, quiet period may be where a patient has minimal movement and is in a specific position.

In various examples, quiet threshold 510 may be modified based on the patient's physical position. For example, utilizing an $A_z$ data point filtered to extract the DC value a person's physical position may be determined. In one example, if the $A_z$ data point has a DC value of 0.5, then the patient is sitting down. In this example, quiet threshold 510 may be increased from the default value of 0.05 to 0.1 to compensate for the difference in the patient's physical position (e.g., sitting down) versus the default patient's physical position (e.g., standing up). In another example, if the $A_z$ data point has a DC value of −1, then the patient is laying down facing up. In this example, quiet threshold 510 may be decreased from the default value of 0.05 to 0.025 to compensate for the difference in the patient's physical position (e.g., laying down facing up) versus the default patient's physical position (e.g., standing up). In another example, the system and/or device may modify one or more algorithms, data, and/or devices to compensate for the patient being in a different position then a default position (e.g., the position that the algorithms, data, and/or devices utilize as a base position).

In FIG. 6, a block diagram of the system and/or the device for validating one or more locations for an external monitoring device 600 is shown, according to one embodiment. In one example, a validation system and/or a validation device may receive one or more data points from one or more of the three anatomical planes (e.g., $A_x$, $A_y$, and $A_z$). In one example, a computing device 601 may include a first high-pass filter 602, a second high-pass filter 604, and a third high-pass filter 606. In addition, computing device 601 may include one or more processors. Computing device 601 may include a first absolute-value filter 608, a second absolute-value filter 610, and a third absolute-value filter 612. Computing device 601 may include a first low-pass filter 614, a second low-pass filter 616, and a third low-pass filter 618. Computing device 601 may include a 3-D magnitude processor 620.

In one example, $A_x$ data may be filtered via first high-pass filter 602, first absolute-value filter 608, and/or first low-pass filter 614, which is then received at 3-D magnitude processor 620. In addition, $A_y$ data may be filtered via second high-pass filter 604, second absolute-value filter 610, and/or second low-pass filter 616, which is then received at 3-D magnitude processor 620. Further, $A_z$ data may be filtered via third high-pass filter 606, third absolute-value filter 612, and/or third low-pass filter 618, which is then received at 3-D magnitude processor 620.

In one example, 3-D magnitude processor 620 may utilize the filtered $A_x$ data, the filtered $A_y$ data, and/or the filtered $A_z$ data to perform a quiet period detection algorithm via a quiet period detection module 622. In this example, a threshold value is inputted to and/or computed by quiet period detection module 622. When the value determined via 3-D magnitude processor 620 based on the filtered $A_x$ data, the filtered $A_y$ data, and/or the filtered $A_z$ data is below the threshold value and/or within the threshold range, then validation system and/or validation device may start looking at one or more outputs (e.g., heart rate data, heart sound data, etc.).

In another example, the validation system and/or validation device may include a baseline filter 624, a heartbeat filter 626, a DC filter 628, and/or a patient position module 630. In one example, the $A_z$ data may be filtered to remove baseline data to extract heart sound data via baseline filter 624, which may produce one or more heart sound signals 634. These one or more heart sound signals 634 may be filtered data. In another example, the filtered heart sound data is inputted to heartbeat filter 626 to produce one or more heart rate data 632. Further, the $A_z$ data may be filtered to extract the DC value via DC filter 628 to produce one or more DC values. The one or more DC values may then be inputted into patient position module 630 to determine one or more positions of the patient.

In various examples, a patient position (e.g., standing up, laying down facing up, laying down facing down, sitting, etc.) may be determined by utilizing one or more data points from the above-referenced planes. For example, utilizing an $A_z$ data point filtered to extract the DC value a person's physical position may be determined. In one example, if the $A_z$ data point has a DC value of 0, then the patient is standing up. In another example, if the $A_z$ data point has a DC value of −1, then the patient is laying down facing up. Further, if the $A_z$ data point has a DC value of 1, then the patient is laying down facing down. This information may be utilized to determine whether the patient is in the right position. If the patient is not in the right position, then the device and/or system may request that the patient move to the right position. For example, an audio and/or visual command may request that the patient move to the correct position. In an example, a message may state, "Please move to a standing up position." In another example, a visual message may read, "Please lay down on the floor looking upward." In another example, the system and/or device may modify one or more algorithms, data, and/or devices to compensate for the patient being in a different position then a default position (e.g., the position that the algorithms, data, and/or devices utilize as a base position). In one example, the $A_z$ value is data obtained normal to the chest.

Figure 7:
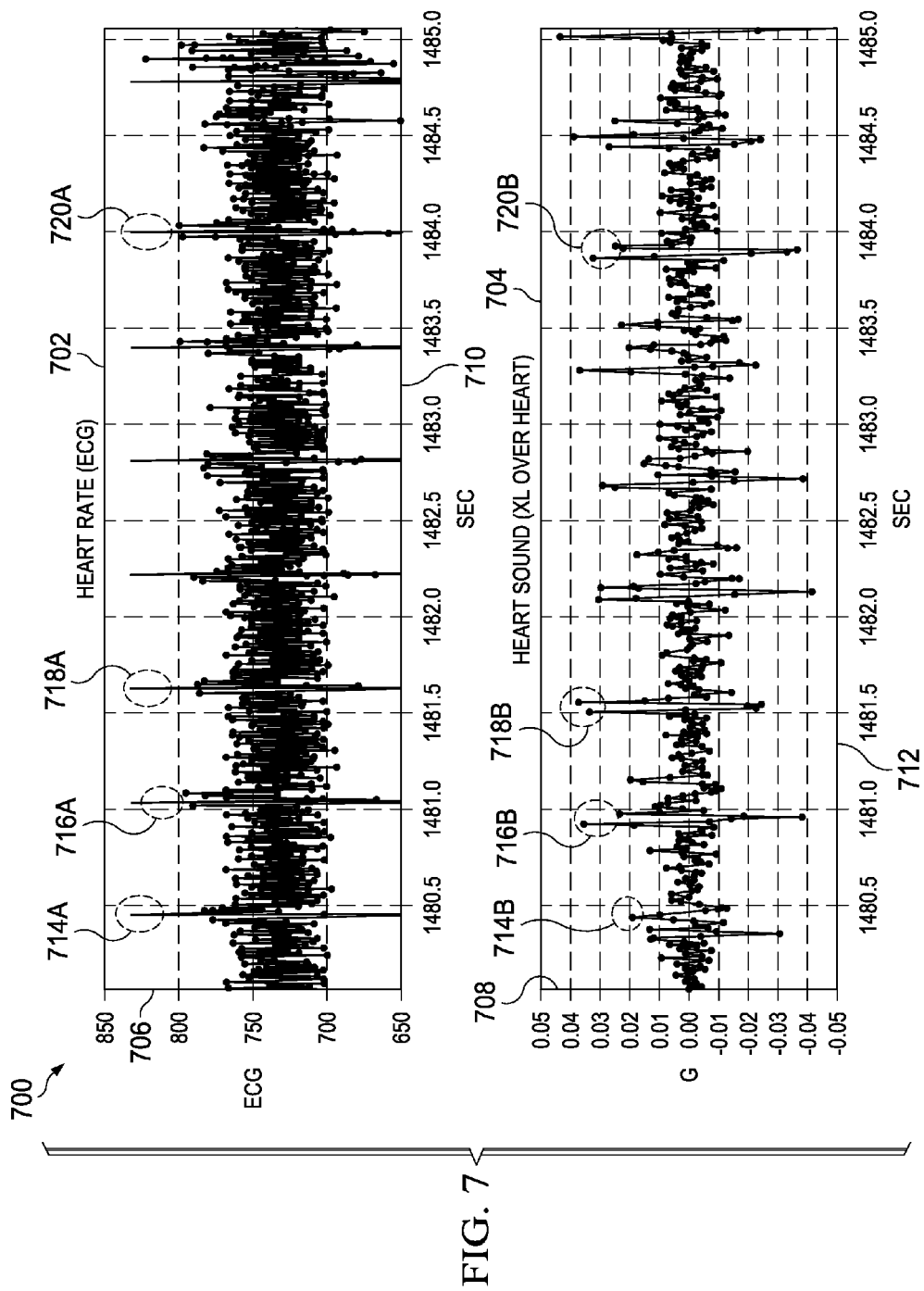
FIG. 7 shows illustrations of data obtained from an electrocardiography signal and a heart sound signal, according to one embodiment.

In FIG. 7, illustrations of data obtained from an ECG signal and a heart sound signal 700 are shown, according to one embodiment. In one example, an ECG graph 702 includes a Y-Axis 706 for ECG data and an X-Axis 710 utilized to plot time. In this example, a heart sound graph 704 includes a Y-Axis 708 for heart sound data and an X-Axis 712 utilized to plot time. In various examples, a first ECG peak 714A correlates with a first heart sound peak 714B. In addition, a second ECG peak 716A correlates with a second heart sound peak 716B. Further, a third ECG peak 718A and an Nth ECG peak 720A correlate with a third heart sound peak 718B and an Nth heart sound peak 720B, respectively.

In one example, the heart rate may be estimated based on the detection of vibration peaks. These vibration peaks may be referenced to a baseline vibration data obtain during one or more quiet period procedures. For example, one or more detected maxima of the signal envelope (e.g., V peaks=first heart sound peak 714B, second heart sound peak 716B, third heart sound peak 718B, and/or an Nth heart sound peak 720B) based on data obtained by the accelerometer may be determined to interrelate to the R peaks (e.g., first ECG peak 714A, second ECG peak 716A, third ECG peak 718A, and/or an Nth ECG peak 720A) of the ECG signal. Therefore, heart rate data may be estimated based on these interrelationships and/or correlations.

In FIG. 8A, a table illustrating various external monitoring device conditions based on data from an ECG signal and a heart sound signal 800A is shown, according to one embodiment. In one example, a first table 800A may include a first heart rate status area 802, a second heart rate status area 804, a monitoring device status area 806, and/or a legend area 808. Legend area 808 may include a not detect status symbol (e.g., X) and a detect status symbol (e.g., O).

In a first condition 810, the first heart rate status is in a non-detected state and the second heart sound status is in a non-detected state, which indicates that the monitoring device status is that the monitoring device is not placed on the patient. (See FIG. 3 reference number 370). In a second condition 812, the first heart rate status is in a detected state and the second heart rate status is in a non-detected state, which indicates that the monitoring device is on the patient, but the monitoring device may not be in the correct location (e.g., exactly over the heart, within the tolerance range, etc.). (See FIG. 3 reference number 368). In a third condition 814, the first heart rate status is in a non-detected state and the second heart rate status is in a detected state, which indicates that the monitoring device is in the correct location and/or within the tolerance range, but the ECG signal and/or the monitoring device integrity may be compromised. (See FIG. 3 reference number 380). In a fourth condition 816, the first heart rate status is in a detected state and the second heart rate status is in a detected state, which indicates that the monitoring device is in the correct location and/or within the tolerance range, along with the ECG signal and/or the monitoring device being in proper working order. (See FIG. 3 reference number 366).

In FIG. 8B, another table illustrating various external monitoring device conditions and/or implantable medical device conditions based on data from an ECG signal and a heart sound signal 800B is shown, according to one embodiment. In one example, a second table 800B may include first heart rate status area 802, second heart rate status area 804, monitoring device status area 806, and/or legend area 808. Legend area 808 may include a not detect status symbol (e.g., X) and a detect status symbol (e.g., O).

In first condition 810, the first heart rate status is in a non-detected state and the second heart sound status is in a non-detected state, which indicates that the monitoring device status is that the monitoring device is not placed on the patient. (See FIG. 3 reference number 370). Further, first condition 810 may indicate that the implantable medical device is not sensing and the device location/orientation has changed. In one example, this may be due to one or more of lead breakage, header misalignment, and/or a patient pulling or twiddling with the device resulting in the device location changing and/or straining of the cuff electrodes. In second condition 812, the first heart rate status is in a detected state and the second heart rate status is in a non-detected state, which indicates that the monitoring device is on the patient, but the monitoring device may not be in the correct location (e.g., exactly over the heart, within the tolerance range, etc.). (See FIG. 3 reference number 368). Further, second condition 812 may indicate that the implantable medical device is sensing, however, the device location and/or orientation has changed which may have implications on the antenna tuning for the relay. In third condition 814, the first heart rate status is in a non-detected state and the second heart rate status is in a detected state, which indicates that the monitoring device is in the correct location and/or within the tolerance range, but the ECG signal and/or the monitoring device integrity may be compromised. (See FIG. 3 reference number 380). Further, third condition 814 may indicate that the implantable medical device has not shifted (e.g., implantable medical device may shift due to the patient twiddling with the device) but the device is not sensing reliably which indicates that there is too much muscle noise (e.g., due to neck and arm movements) and/or the leads are compromised. In fourth condition 816, the first heart rate status is in a detected state and the second heart rate status is in a detected state, which indicates that the monitoring device is in the correct location and/or within the tolerance range, along with the ECG signal and/or the monitoring device being in proper working order. (See FIG. 3 reference number 366). Further, fourth condition 816 may indicate that the implantable medical device is sensing reliably.

In one example, the external monitoring device located on a patient may include one or more processors, one or more memory devices, one or more power devices, one or more heart rate detection devices, and one or more heart sound detection devices. In one example, at least one of the one or more heart sound detection devices may be an accelerometer.

In another example, the external monitoring device may include a validation module. The validation module may determine a plurality of external monitoring device conditions based on heart rate data and heart sound data. In another example, the one or more processors may determine via the validation module a first external monitoring device condition. The first external monitoring device condition may be that the external monitoring device has not been placed on the patient. In another example, the one or more processors may determine via the validation module a second external monitoring condition. The second external monitoring condition may be that the external monitoring device is misaligned on the patient. In one example, the one or more processors may determine via the validation module a third external monitoring condition. The third external monitoring condition may be that an error has occurred on a patch and/or with the electrocardiography signal. In another example, the one or more processors may determine via the validation module a fourth external monitoring condition. The fourth external monitoring condition may be that the external monitoring device is located in a tolerance range and working properly.

In another example, the method for determining a status of an external monitoring device located on a patient may include: obtaining via one or more processors heart rate data; obtaining via the one or more processors heart sound data; and/or determining via the one or more processors an external monitoring device state via a validation module based on the heart rate data and the heart sound data. In another example, the method may include determining a location of the external monitoring device and/or modifying the validation module based on a determined external monitoring device location. In another example, the method may include determining the external monitoring device state via an adjusted validation module based on the heart rate data and the heart sound data. In addition, the method may include determining a first external monitoring device condition. The first external monitoring device condition may be that the external monitoring device has not been placed on the patient. Further, the method may include determining a second external monitoring condition. The second external monitoring condition may be that the external monitoring device is misaligned on the patient. In addition, the method may include determining a third external monitoring condition. The third external monitoring condition may be that an error has occurred on a patch and/or with the electrocardiography signal. Further, the method may include determining a fourth external monitoring condition. The fourth external monitoring condition may be that the external monitoring device is located in a tolerance range.

Alternatively, table 800 may include a heart rate status area 802, a heart sound status area 804, monitoring device status area 806, and/or legend area 808. Legend area 808 may include a not detected status symbol (e.g., X) and a detected status symbol (e.g., 0).

In a first condition 810, the heart rate status is in a non-detected state and the heart sound status is in a non-detected state, which indicates that the monitoring device status is that the monitoring device is not placed on the patient. In a second condition 812, the heart rate status is in a detected state and the heart sound status is in a non-detected state, which indicates that the monitoring device is on the patient, but the monitoring device may not be in the correct location (e.g., exactly over the heart, within the tolerance range, etc.). In a third condition 814, the heart rate status is in a non-detected state and the heart sound status is in a detected state, which indicates that the monitoring device is in the correct location and/or within the tolerance range, but the ECG signal and/or the monitoring device integrity may be compromised. In a fourth condition 816, the heart rate status is in a detected state and the heart sound status is in a detected state, which indicates that the monitoring device is in the correct location and/or within the tolerance range, along with the ECG signal and/or the monitoring device being in proper working order.

In one example, the external monitoring device located on a patient may include one or more processors, one or more memory devices, one or more power devices, one or more heart rate detection devices, and one or more heart sound detection devices. In one example, at least one of the one or more heart sound detection devices may be an accelerometer. In another example, the external monitoring device may include a validation module. The validation module may determine a plurality of external monitoring device conditions based on heart rate data and heart sound data. In another example, the one or more processors may determine via the validation module a first external monitoring device condition. The first external monitoring device condition may be that the external monitoring device has not been placed on the patient. In another example, the one or more processors may determine via the validation module a second external monitoring condition. The second external monitoring condition may be that the external monitoring device is misaligned on the patient. In one example, the one or more processors may determine via the validation module a third external monitoring condition. The third external monitoring condition may be that an error has occurred on a patch and/or with the electrocardiography signal. In another example, the one or more processors may determine via the validation module a fourth external monitoring condition. The fourth external monitoring condition may be that the external monitoring device is located in a tolerance range.

In another example, the method for determining a status of an external monitoring device located on a patient may include: obtaining via one or more processors heart rate data; obtaining via the one or more processors heart sound data; and/or determining via the one or more processors an external monitoring device state via a validation module based on the heart rate data and the heart sound data. In another example, the method may include determining a location of the external monitoring device and/or modifying the validation module based on a determined external monitoring device location. In another example the method may include determining the external monitoring device state via an adjusted validation module based on the heart rate data and the heart sound data. In addition, the method may include determining a first external monitoring device condition. The first external monitoring device condition may be that the external monitoring device has not been placed on the patient. Further, the method may include determining a second external monitoring condition. The second external monitoring condition may be that the external monitoring device is misaligned on the patient. In addition, the method may include determining a third external monitoring condition. The third external monitoring condition may be that an error has occurred on a patch and/or with the electrocardiography signal. Further, the method may include determining a fourth external monitoring condition. The fourth external monitoring condition may be that the external monitoring device is located in a tolerance range.

Figure 9A:
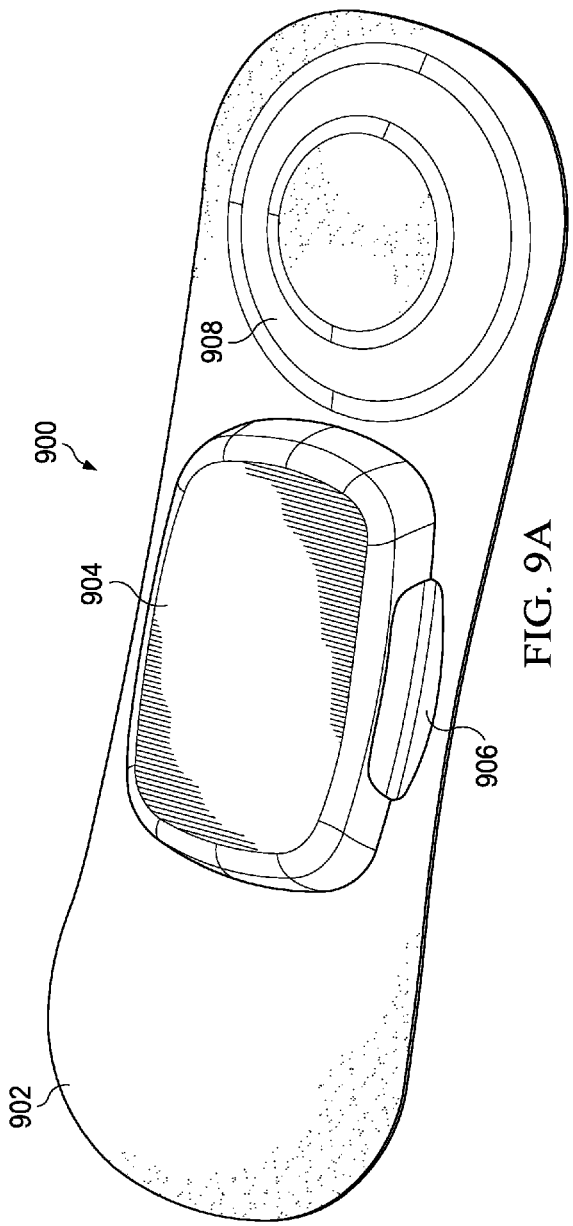
FIGS. 9A-9B are illustrations of the external monitoring device, according to various embodiments.

In FIG. 9A, a first external monitoring device illustration 900 is shown, according to one embodiment. An external monitoring device 902 may include a sensing device 904 attached via one or more attachment devices 906 to external monitoring device 902. External monitoring device 902 and/or sensing device 904 may be powered by one or more power sources 908.

Figure 9B:
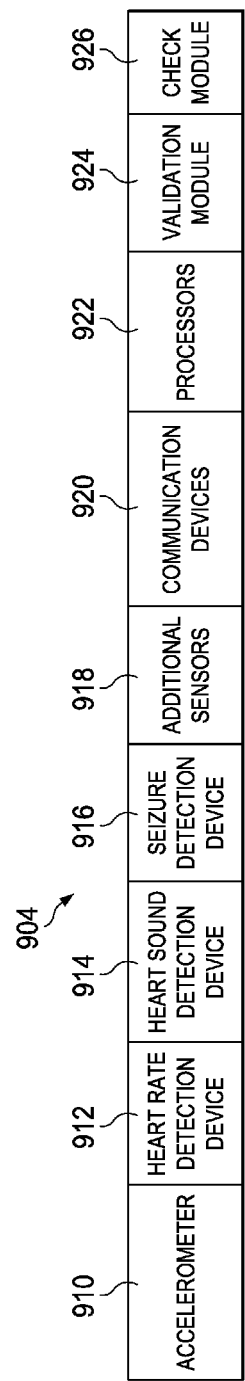

FIG. 9B illustrates that sensing device 904 may include an accelerometer 910, one or more heart rate detection devices 912, one or more additional heart sound detection devices 914, one or more seizure detection devices 916, one or more additional sensors 918, one or more communication devices 920, one or more processors 922, a validation module 924, and/or a check module 926. Any element of sensing device 904 and/or monitoring device 102 may communicate with any external device (e.g., a server, a base station, a mobile device, a computer, etc.). These communicates may relate to any patient and/or device activity. One or more devices may transmit and receive information relating to seizure history, the onset of a seizure, any characteristics of an active and/or historical seizure, heart rate data, heart sound data, therapy history, current therapy, medication history, current medication, family health history, any characteristics of one or more therapies, blood pressure, any other patient characteristic, and/or any device characteristic (e.g., service history, battery life, installed date, efficiency, power consumption, duty cycle, etc.). Validation module 924 may generate, initiate, compile, store, and/or transmit any data and/or procedure related to any validation process disclosed in this disclosure.

In FIG. 10, a flow chart for validating the location of one or more external devices 1000 is shown, according to one embodiment. The method may include determining which type of heart rate detection device is being utilized (step 1010). The method may include one or more processors determining whether check module 926 needs to be modified based on the type of heart rate detection device (step 1020). If check module 926 does not need to be modified, then the method may move to step 1040. If check module 926 does need to be modified, then the method may include adjusting check module 926 based on the type of heart rate detection device being utilized (step 1030). The method may include determining which type of heart sound detection device is being utilized (step 1040). The method may include one or more processors determining whether check module 926 needs to be modified based on the type of heart sound detection device (step 1050). If check module 926 does not need to be modified, then the method may utilize check module 926 (step 1070). If check module 926 does need to be modified, then the method may include adjusting check module 926 based on the type of heart sound detection device being utilized (step 1060) and utilizing check module 926 (step 1070).

For example, a first type of heart rate detection device and a first type of heart sound detection device may be the base heart rate detection device and the base heart sound detection device, respectively. In one example, a second type of heart rate detection device may require a first modification to check module 926 (e.g., default check module). In another example, a third type of heart rate detection device may require a second modification to the default check module. In another example, an Nth type of heart rate detection device may require an Nth modification to the default check module.

In another example, a second type of heart sound detection device may require a third modification to the default check module. Further, a third type of heart sound detection device may require a fourth modification to the default check module. Whereas, an Nth type of heart sound detection device may require an Nth modification to the default check module. Check module 926 and validation module 924 may be combined into one module.

Figure 11:
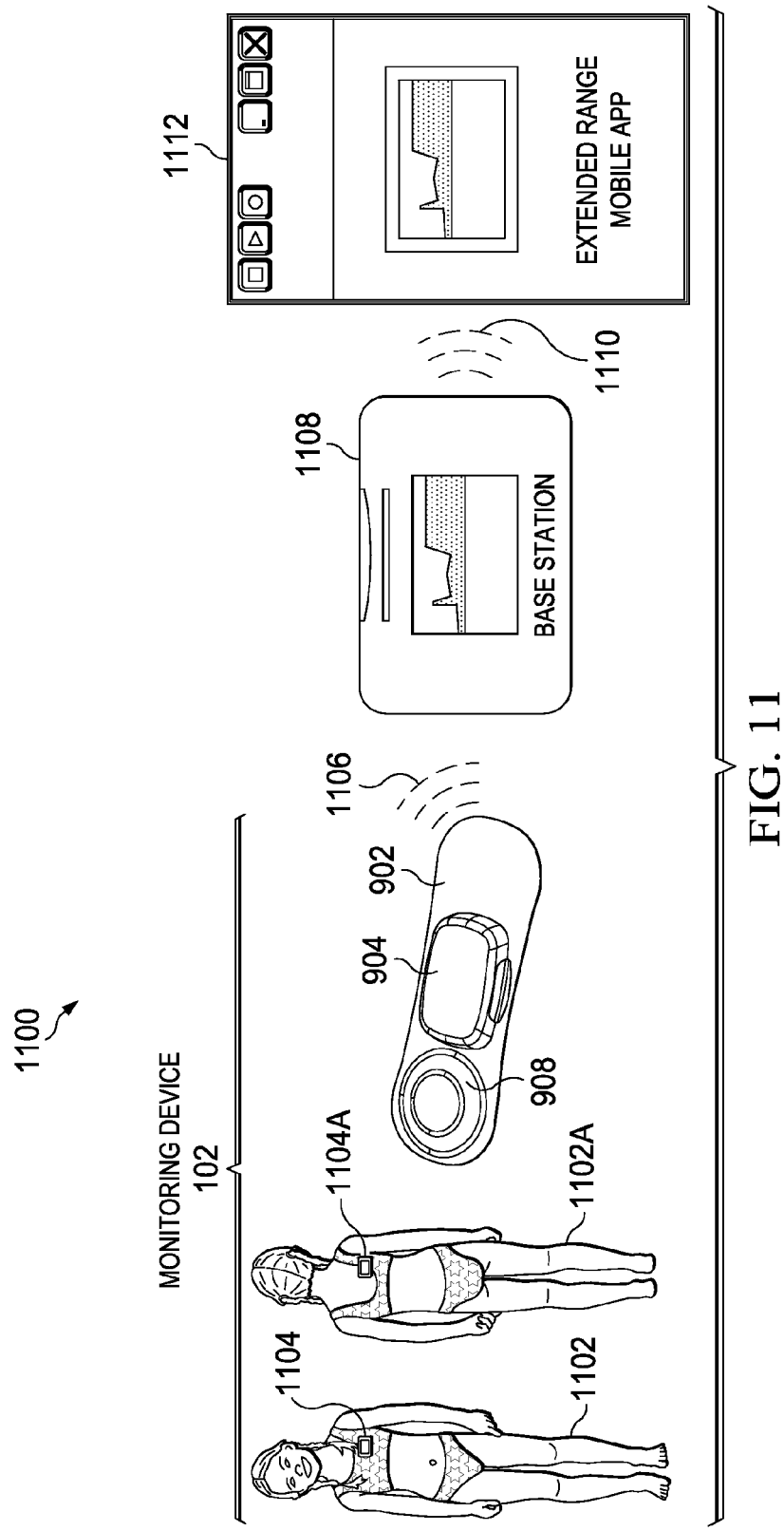
FIG. 11 is an illustration of a monitoring system, according to one embodiment.

In FIG. 11, an illustration of a monitoring system 1100 is shown, according to one embodiment. Monitoring system 1100 may include monitoring device 102 being located at a first position 1104 on the front of a patient 1102, monitoring device 102 being located at a second position 1104A on the back of a patient 1102A, and/or monitoring device 102 being located at any location on any part of a patient. Monitoring device 102 may include sensing device 904 and one or more power sources 908 (see FIGS. 9A and 9B). Monitoring device 102 may communicate via a first communication link 1106 with a base station 1108. Base station 1108 may communicate via a second communication link 1110 with one or more computing devices 1112. One or more computing devices 1112 may be a server, a computer, a mobile device, a TV, and/or any other computing device capable of communicating with base station 1108 and/or monitoring device 102. Monitoring device 102 may communicate directly and/or indirectly (e.g., from first communication link 1106 to second communication link 1110 to Nth communication link) with any computing device, including one or more computing devices 1112.

In one example, the system may include an external monitoring device located on a patient. The external monitoring device may include one or more processors, one or more memory devices, one or more power devices, one or more heart rate detection devices, and/or one or more heart sound detection devices. The system may further include a base station, which may include a base station processor, a base station memory, and a base station power supply. In addition, the system may include an external device, which may include an external device processor, an external device memory, and an external device power supply. In one example, the system may include an accelerometer as one of the heart sound detection devices. Further, the external monitoring device may include a validation module. The validation module may determine a plurality of external monitoring device conditions based on heart rate data and heart sound data. In another example, the one or more processors of the external monitoring device may determine via the validation module a first external monitoring device condition. The first external monitoring device condition may be that the external monitoring device has not been placed on the patient. In another example, the one or more processors of the external monitoring device may determine via the validation module a second external monitoring condition. The second external monitoring condition may confirm that the external monitoring device is misaligned on the patient. In one example, the one or more processors of the external monitoring device may determine via the validation module a third external monitoring condition. The third external monitoring condition may be that an error has occurred on at least one of a patch and an electrocardiography signal. In one example, the one or more processors of the external monitoring device may determine via the validation module a fourth external monitoring condition. The fourth external monitoring condition may be that the external monitoring device is located in a tolerance range and working properly.

In another embodiment, an implantable medical system may include an implantable medical device and an external monitoring device. The external monitoring device may include one or more processors, one or more memory devices, one or more power devices, one or more heart rate detection devices, and one or more heart sound detection devices. In addition, one or more of the heart sound detection devices may be an accelerometer. In another example, the external monitoring device may include a validation module. The validation module may determine a plurality of conditions based on heart rate data and heart sound data. Further, the external monitoring device may determine an implantable medical device orientation (and/or any other devices orientation including itself). In addition, the external monitoring device may determine an implantable medical device orientation based on at least one of the plurality of conditions. In another example, the external monitoring device may modify one or more antenna characteristics. In another example, the external monitoring device may modify one or more antenna characteristics based on one or more of the plurality of conditions.

Figure 12:
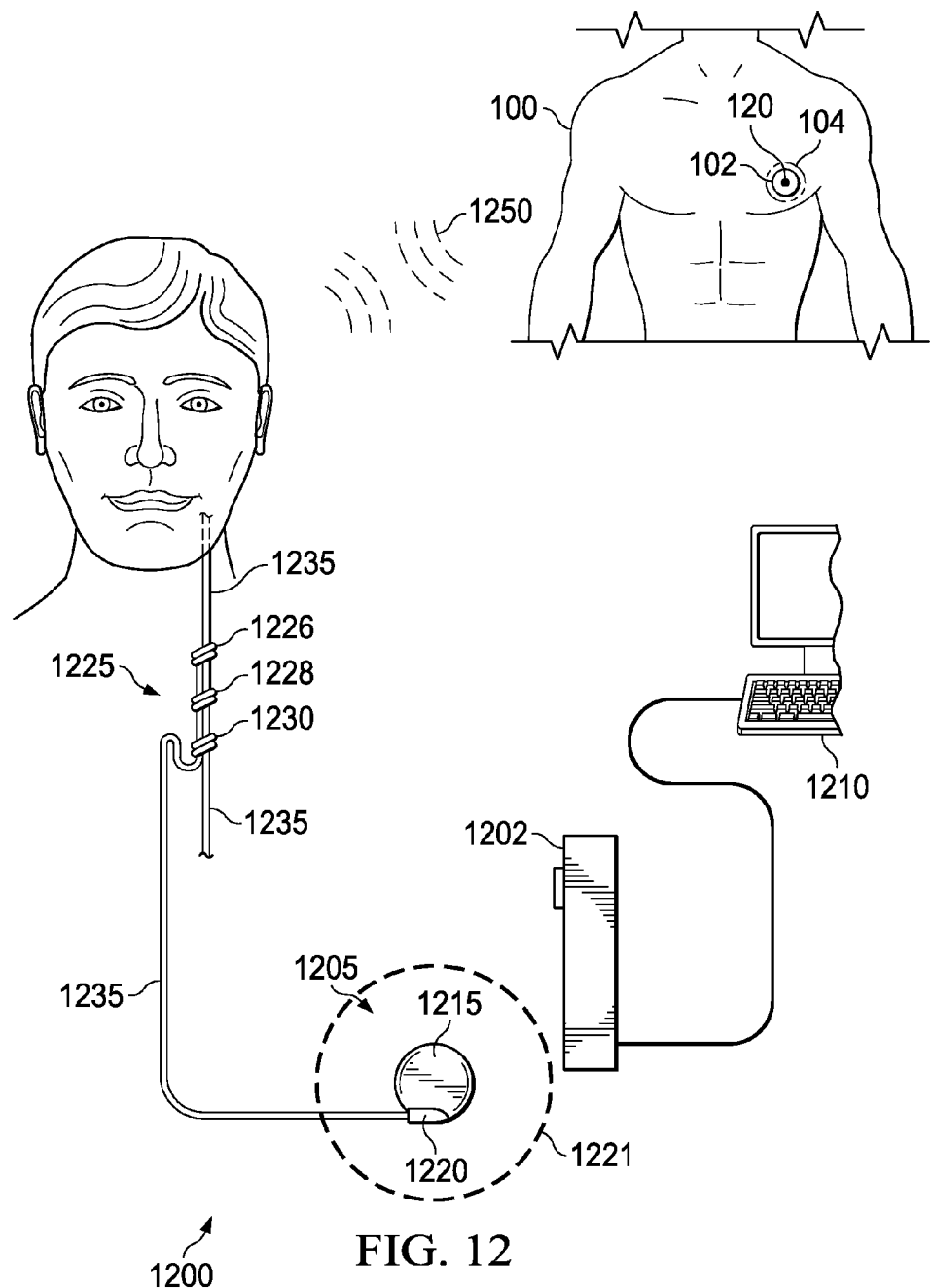
FIG. 12 is an illustration of an implantable medical device, according to one embodiment.

In FIG. 12, an illustration of an implantable medical device 1200 is shown, according to one embodiment. In this example, implantable medical system ("IMD") 1200 may include an electrical signal generator 1205. Electrical signal generator 1205 may include a main body 1215, including a case or shell with a header 1220 for connecting to an insulated, electrically conductive lead assembly 1235. Electrical signal generator 1205 may be implanted in the patient's chest in a pocket or cavity formed by the implanting surgeon just below the skin (indicated by a dotted line 1221). Monitoring device 102 may communicate via a third communication link 1250 with IMD 1200. For example, monitoring device 102 and IMD 1200 may transmit and receive information relating to seizure history, the onset of a seizure, any characteristics of any current and/or historical seizure, heart rate data, heart sound data, therapy history, current therapy, medication history, current medication, family health history, any characteristics of any therapy, blood pressure, duty cycle, any other element relating to the patient and/or any other element relating to any other device.

In various examples, the decision trees shown in FIGS. 8A-8B may be utilized with an implantable medical device and/or the external monitoring system. In various examples, the conditions described in FIGS. 8A-8B may ensure the reliable sensing of the implantable medical device, the external monitoring device, and/or any other device. Further, the RF communication performance may be enhanced by keeping track of one or more device (e.g., implantable medical device, external monitoring device, etc.) orientations. Further, this disclosure may be used in conjunction with a tracking filter, such as a Kalman filter, extended Kalman filter, particle filters, and/or an unscented Kalman filter to continuously track one or more positions and/or orientations of one or more devices.

A nerve electrode assembly 1225 may include a plurality of electrodes having at least an electrode pair conductively connected to the distal end of lead assembly 1235, which may include a plurality of lead wires (one wire for each electrode). Each electrode in nerve electrode assembly 1225 may operate independently or alternatively, may operate in conjunction with the other electrodes. In one embodiment, nerve electrode assembly 1225 may include at least a cathode and an anode. In another embodiment, nerve electrode assembly 1225 comprises one or more unipolar electrodes with the return electrode including a portion of electrical signal generator 1205.

Lead assembly 1235 is attached at its proximal end to connectors on a header 1220 of electrical signal generator 1205. Nerve electrode assembly 1225 may be surgically coupled to a vagus nerve 1235 in the patient's neck or at another location (e.g., near the patient's diaphragm or at the esophagus/stomach junction, etc.). Other and/or additional cranial nerves, such as the trigeminal and/or glossopharyngeal nerves, may also be used as a target for the electrical signal in particular alternative embodiments. In one embodiment, nerve electrode assembly 1225 comprises a bipolar stimulating electrode pair 1226, 1228, 1230 (i.e., a cathode and an anode). Suitable electrode assemblies are available from Cyberonics, Inc., Houston, Tex., USA as the Model 302 electrode assembly. However, persons of skill in the art will appreciate that many electrode designs could be used in the present disclosure. Lead assembly 1235 may be secured, while retaining the ability to flex with movement of the chest and neck, by a suture connection to nearby tissue (not shown).

In alternative embodiments, nerve electrode assembly 1225 may comprise temperature sensing elements and/or heart rate sensor elements. Other sensors for other body parameters may also be employed to trigger active stimulation. For example, motion sensors or electrodes may be used to sense respiration, and pressure sensors or neural activity may be used to sense blood pressure. Both passive and active stimulation may be combined or delivered by a single IMD according to the present disclosure. Either or both modes may be appropriate to treat a specific patient under observation.

Electrical pulse generator 1205 may be programmed with an external device ("ED") such as a computer 1210, base station 1108, monitoring device 102, a mobile device, and/or one or more computing devices 1112 using programming software. A programming wand 1202 and/or another programming device may be coupled to computer 1210 as part of the ED to facilitate radio frequency ("RF") communication between computer 1210 and electrical pulse generator 1205. Programming wand 1202 and computer 1210 (and/or base station 1108, monitoring device 102, a mobile device, and/or one or more computing devices 1112) permit non-invasive communication with electrical signal generator 1205 after the latter is implanted. In systems where computer 1210 uses one or more channels in the Medical Implant Communications Service ("MICS") bandwidths, programming wand 1202 may be omitted to permit more convenient communication directly between computer 1210 (and/or base station 1108, monitoring device 102, a mobile device, and/or one or more computing devices 1112) and electrical pulse generator 1205.

The term "electrode" or "electrodes" described herein may refer to one or more stimulation electrodes (i.e., electrodes for delivering an electrical signal generated by an IMD to a tissue), sensing electrodes (i.e., electrodes for sensing a physiological indication of a patient's body), and/or electrodes that are capable of delivering a stimulation signal, as well as performing a sensing function.

Cranial nerve stimulation has been proposed to treat a number of medical conditions pertaining to or mediated by one or more structures of the nervous system of the body, including epilepsy and other movement disorders, depression, anxiety disorders and other neuropsychiatric disorders, dementia, head trauma and traumatic brain injury, coma, obesity, eating disorders, sleep disorders, cardiac disorders (such as congestive heart failure and atrial fibrillation), hypertension, endocrine disorders (such as diabetes and hypoglycemia), and pain syndromes (including migraine headache and fibromyalgia), among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the numerous disorders for which cranial nerve stimulation has been proposed or suggested as a treatment option, the fact that detailed neural pathways for many (if not all) cranial nerves remain relatively unknown, makes predictions of efficacy for any given disorder difficult or impossible. Moreover, even if such pathways were known, the precise stimulation parameters that would modulate particular pathways relevant to a particular disorder generally cannot be predicted.

In one embodiment, the present disclosure provides a method of treating a medical condition. The medical condition can be selected from the group including epilepsy, neuropsychiatric disorders including, but not limited to, depression, eating disorders/obesity, traumatic brain injury/coma, addiction disorders, dementia, sleep disorders, pain, migraine, fibromyalgia, endocrine/pancreatic disorders (including, but not limited to, diabetes), motility disorders, hypertension, congestive heart failure/cardiac capillary growth, hearing disorders, angina, syncope, vocal cord disorders, thyroid disorders, pulmonary disorders, and reproductive endocrine disorders including infertility. In a particular embodiment, the medical condition is epilepsy.

The implantable medical device ("IMD") system of one embodiment of the present disclosure provides for software module(s) that are capable of acquiring, storing, and processing various forms of data, such as patient data/parameters (e.g., physiological data, side-effects data, such as heart rate, breathing rate, brain-activity parameters, disease progression or regression data, quality of life data, etc.) and therapy parameter data. Therapy parameters may include, but are not limited to, electrical signal parameters that define the therapeutic electrical signals delivered by the IMD, medication parameters and/or any other therapeutic treatment parameter. In an alternative embodiment, the term "therapy parameters" may refer to electrical signal parameters defining the therapeutic electrical signals delivered by the IMD. Therapy parameters for a therapeutic electrical signal may also include, but are not limited to, a current amplitude, a pulse width, an interburst period, a number of pulses per burst, an interpulse interval, a burst duration, an on-time, and an off-time.

In one embodiment of the present disclosure, an electrical signal may be provided in a duration that is determined as a function of a physiological cycle (e.g., a cardiac cycle). In one embodiment, the duration may be less than the physiological cycle (e.g., less than a cardiac cycle of the patient). In this manner, data relating to a parameter associated with the physiological cycle may be collected at times when the electrical signal is not provided. For example, by providing electrical signals to a vagus nerve 10 msec after detection of an R-wave in a patient's cardiac cycle, for a duration that is less than the prior cardiac cycle, it may be possible to sense the next R-wave without interference that may be associated with a signal applied for a duration longer than the patient's cardiac cycle. While techniques are available that would permit overlapping stimulation and sensing (such as blanking intervals in the signal, or use of separate sensing and stimulation electrodes), use of certain embodiments of the present disclosure renders such techniques unnecessary, and permits a simpler design. Even where stimulation durations longer than the cardiac cycle are used, the present disclosure may still allow the timing of later heartbeats to be predicted with sufficient accuracy (based on, for example, a moving average heartbeat) to avoid the use of separate sensing and stimulation electrodes.

The therapeutic electrical stimulation signal described herein may be used to treat a medical condition separately or in combination with another type of treatment. For example, electrical signals according to the present disclosure may be applied in combination with a chemical agent, such as various drugs, to treat various medical conditions. Further, the electrical stimulation may be performed in combination with treatment(s) relating to a biological or chemical agent. The electrical stimulation treatment may also be performed in combination with other types of treatment, such as magnetic stimulation treatment.

Particular embodiments may provide effective screening tools to determine whether a particular type of treatment will be effective for a particular patient. Disclosed implantable medical devices may be used to treat various conditions by applying treatment to one or more tissues of a patient's body. To illustrate, an implantable medical device may be used to target neural tissue by inducing efferent or afferent action potentials in the neural tissue or by blocking intrinsic efferent or afferent action potentials in the neural tissue. For example, the implantable medical device may be used to target a vagus or trigeminal nerve to treat one or more conditions, such as epilepsy or other seizure inducing conditions. In another example, the implantable medical device may target an optic nerve to treat a vision condition or to supplement or facilitate use of a visual prosthesis for sight restoration. In another example, the implantable medical device may target a hypoglossal nerve to treat one or more conditions, such as sleep apnea. Although the examples above each relate to cranial nerves, the implantable medical device may be used to target another nerve or set of nerves rather than or in addition to a cranial nerve. For example, the implantable medical device may be used to target a sacral nerve to treat one or more conditions, such as to facilitate bladder control. In another example, the implantable medical device may be used to target a phrenic nerve to treat one or more conditions, such as to facilitate diaphragm or respiration control. In another example, the implantable medical device may be used to target one or more nerves of the spinal cord to treat one or more conditions, such as to facilitate pain management. Further, in addition to or instead of targeting a neural tissue, the implantable medical device may be used to target other tissue of a patient's body. For example, the implantable medical device may be used to stimulate a muscle to induce muscle contraction. To illustrate, the implantable medical device may target a heart muscle to act as a pacemaker. Other examples of conditions that may be treated using an implantable medical device that is at least partially powered by far field radiative power include, but are not limited to, traumatic brain injury and depression.

In various examples, monitoring device 102, base station 1108, implantable medical device 1302, and/or one or more computing devices 1112 may interact to provide one or more functions. For example, base station 1108 may be the lead device to perform one or more calculations and/or to generate one or more items (e.g., reports, status updates, etc.). In various examples, any device (e.g., monitoring device 102, base station 1108, implantable medical device 1302, and/or one or more computing devices 1112) may be the lead device to perform one or more computational functions. Further, the one or more computational functions may be shared and/or distributed over any of the above-referenced devices. In another example, monitoring device 102 may transmit one or more data points (e.g., heart sound data, heart rate data, skin temperature data, seizure detection, any other patient physical condition, etc.) to implantable medical device 1302 (and/or any other device) to assist in seizure detection, therapy feedback, etc. In another example, implantable medical device 1302 may transmit one or more data points (e.g., seizure detection, heart rate, blood pressure, any other patient physical condition, etc.) to monitoring device 102 (and/or any other device) to assist in seizure detection, generation and transmission of one or more warning messages, generation of one or more historical reports, etc. In another example, one or more computing devices 1112 may receive various data points (e.g., heart sound data, heart rate data, skin temperature data, seizure detection, blood pressure, any other patient physical condition, etc.) to generate and transmit one or more programming modifications to one or more of the other devices (e.g., monitoring device 102, base station 1108, implantable medical device 1302, etc.).

Figure 13:
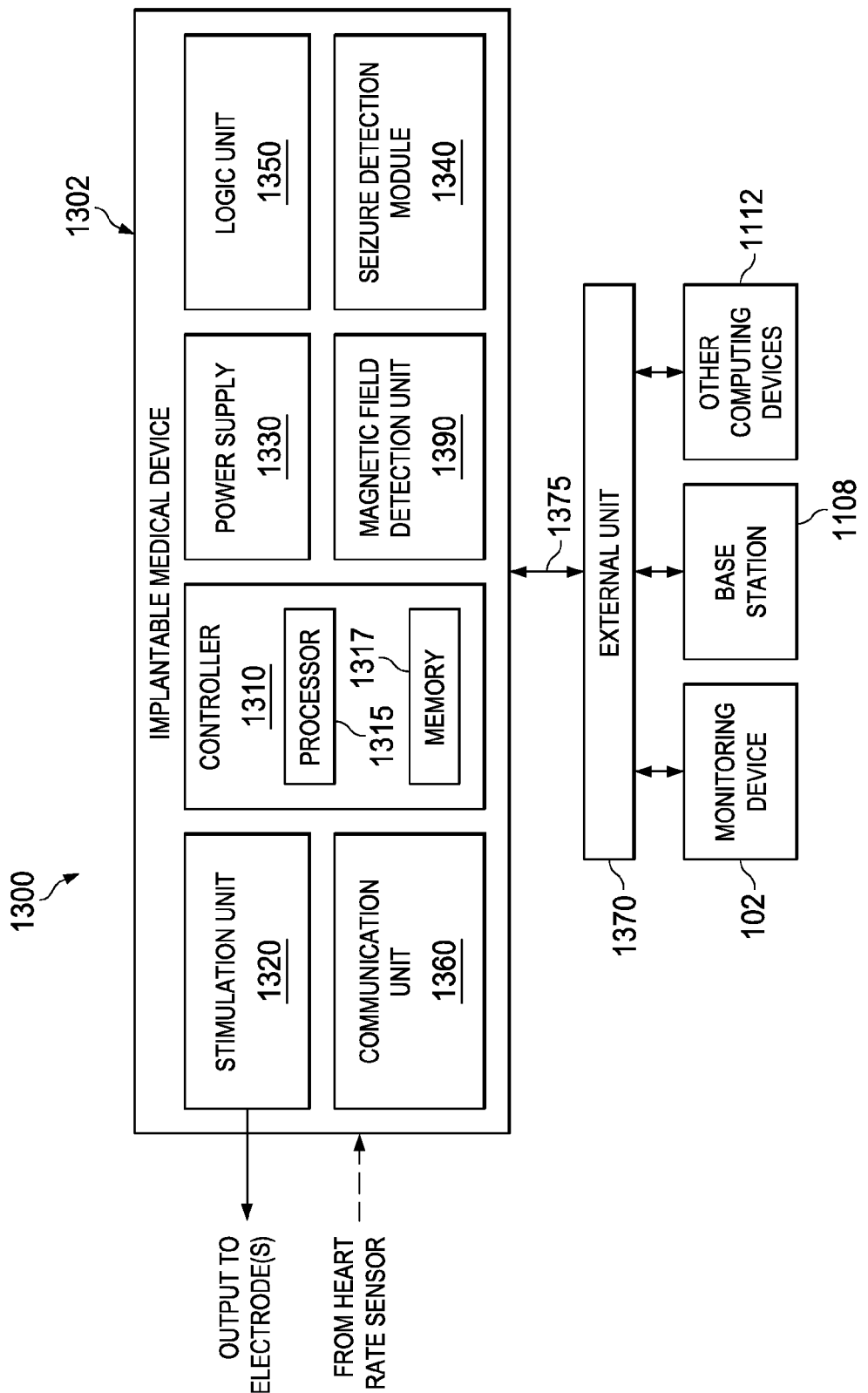
FIG. 13 is a block diagram of an implantable medical device, according to one embodiment.

In FIG. 13, a block diagram of an implantable medical device system 1300 is shown, according to one embodiment. Implantable medical device system 1300 may include an implantable medical device 1302 and an external device 1370. Implantable medical device 1302 may be wirelessly powered by external device 1370. For example, external device 1370 may emit electromagnetic energy by transmitting radio-frequency signals using an external antenna (e.g., a far field transmitter, etc.). At least a portion of the electromagnetic energy may be received by an antenna of implantable medical device 1302 as far field radiative signals. In another example, implantable medical device 1302 may receive energy via near-field signals (e.g., by inductive coupling of the antenna of implantable medical device 1302 and an antenna of the far field transmitter). In yet another example, implantable medical device 1302 may receive energy via near-field signals and via far field radiative signals, either simultaneously or at different times. In various examples, monitoring device 102, base station 1108, implantable medical device 1302, and/or one or more computing devices 1112 may be supplied energy via any of the energy transfer procedures discussed in this disclosure.

As further described below, implantable medical device 1302 may include an antenna to receive the far field radiative signals, a matching network to impedance match the antenna with other components of implantable medical device 1302, power processing elements (e.g., a rectifier, a voltage multiplier, a step-up regulator, etc.), a charge storage element, and a therapy deliver unit. Implantable medical device 1302 may use power derived at least partially from the far field radiative signals to deliver therapy to a patient.

In a particular embodiment, implantable medical device 1302 (and/or monitoring device 102, base station 1108, one or more computing devices 1112, etc.) may include an antenna and an associated matching network. The antenna may be a dipole antenna, a monopole antenna, a serpentine antenna, a slot antenna, a patch antenna, a plane-inverted-F antenna ("PIFA"), a helical antenna, a fractal antenna, a loop antenna, or an antenna with another form factor configured to receive the far field radiative signals. The matching network may be adapted to match impedance of the antenna to other components of implantable medical device 1302 (and/or monitoring device 102, base station 1108, one or more computing devices 1112, etc.) to achieve high efficiency power transfer.

Implantable medical device 1302 may include a stimulation unit 1320, a communication unit 1360, a controller 1310, one or more processors 1315, a memory 1317, a power supply 1330, a magnetic field detection unit 1390, a logic unit 1350, and/or a seizure detection module 1340.

Stimulation unit 1320 may be powered by one or more charge storage elements. Stimulation unit 1320 may be operative to deliver therapy to a target tissue of the patient. For example, stimulation unit 1320 may include a signal generator that is operative to apply electrical stimulation to the target tissue. In another example, stimulation unit 1320 is a drug delivery unit that is operative to deliver a drug as the therapy to the patient. The target tissue may include neural tissue (e.g., one or more areas of the brain, the spinal cord, a cranial nerve, or another nerve), muscular tissue (e.g., a heart muscle), and/or other tissue. In a particular embodiment, the target tissue includes one or more of a vagus nerve, a trigeminal nerve, a glossopharyngeal nerve, and a hypoglossal nerve.

In a particular embodiment, the charge storage element may be sized or configured to store only enough charge to deliver the therapy during a short time period relative to typically implantable medical device batteries. To illustrate, the charge storage element may store enough charge to deliver the therapy during a period of 3 days or less. In another example, the charge storage element may store enough charge to deliver the therapy during a period of 24 hours or less. In other examples, the charge stored by the charge storage element is sufficient to deliver the therapy during a period of 12 hours or less, during a period of 6 hours or less, during a period of 3 hour or less, during a period of 2 hour or less, during a period of 1 hour or less, during a period of 30 minutes or less, during a period of 15 minutes or less, during a period of 10 minutes or less, during a period of 5 minutes or less, during a period of 2 minutes or less, during a period of 1 minutes or less, during a period of 30 seconds or less, or even during a period of 15 seconds or less. In a particular embodiment, the charge storage element 114 stores enough charge to deliver only a single treatment. The single treatment may be a single electrical pulse, or a burst including a plurality of electrical pulses.

In implantable medical device 1302, stimulation unit 1320 is a signal generator. The signal generator may be operative to be electrically coupled to one or more electrodes. The electrode(s) may be configured to be positioned in proximity to, or attached to, the target tissue of the patient to provide electrical stimulation to the target tissue. The electrodes(s) may be coupled directly to implantable medical device 1302 (i.e., without leads) or may be coupled to implantable medical device 1302 via one or more leads (not shown).

Implantable medical device 1302 may include logic unit 1350. Logic unit 1350 may be powered by the charge storage element. Logic unit 1350 may be operative to control delivery of the therapy by stimulation unit 1320. For example, logic unit 1350 may control parameters of therapeutic stimulation provided by the signal generator to the target tissue. The parameters of the therapeutic stimulation may include a frequency of therapy delivery (i.e., a time period between treatments), a duty cycle of therapy delivery, a magnitude of therapy delivery (e.g., an amount of energy delivered to the target tissue during a treatment, a magnitude of a voltage of an electrical signal used to deliver the therapy, a magnitude of a current of the electrical signal, or a combination thereof), and a mode of therapy delivery (e.g., a single pulse mode or a burst mode including a plurality of pulses). Other parameters may also be controlled by logic unit 1350, such as a location treated when more than one target tissue can be selected for treatment; whether the treatment includes electrical stimulation, delivery of a drug, other treatment, or a combination thereof; and whether electrical signals applied to the target tissue induce efferent signals, induce afferent signals, bias the target tissue to near a firing threshold, inhibit intrinsic efferent or afferent signals, and so forth.

In a particular embodiment, logic unit 1350 may cause the therapeutic stimulation to be applied to the target tissue responsive to a sensed patient parameter (e.g., a condition, state or value associated with the body of the patient). For example, logic unit 1350 may receive information via one or more of the electrodes, from another sensor, monitoring device 102, base station 1108 and/or one or more computing devices 1112, and may control application of therapeutic stimulation based on the received information. Therapeutic stimulation that is based on or responsive to the sensed patient parameter may include "active," "responsive," "closed-loop," "feedback," or "triggered" stimulation.

In another embodiment, logic unit 1350 may cause the therapeutic stimulation to be applied to the target tissue without sensing or detecting a patient parameter. For example, logic unit 1350 may cause the signal generator to apply a series of electrical pulses to the target tissue periodically, intermittently, or continuously throughout the day, or according to another predetermined schedule (e.g., a circadian schedule or another predetermined treatment cycle). This type of stimulation may include "passive," "periodic," "continuous," "open-loop," "non-feedback," or "prophylactic" stimulation. In another embodiment, logic unit 1350 may use a combination of active, passive and externally controlled stimulation. For example, in response to receipt of the far field radiative signals, logic unit 1350 may initiate stimulation responsive to a sensed patient parameter (e.g., sensing one or more patient parameters and applying stimulation responsive to the one or more sensed patient parameters). In another embodiment, the charge threshold may be set according to an amount of charge needed to deliver more than one treatment, such as a number of treatments specified for a particular amount of time, such as at least 3 days, at least 1 day, at least 12 hours, at least 6 hours, at least 3 hours, at least 2 hours, at least 1 hour, at least 30 minutes, at least 15 minutes, at least 10 minutes, at least 5 minutes, at least 2 minutes, at least 1 minute, at least 30 seconds, at least 15 seconds, at least 10 seconds, or less than 10 seconds. In this embodiment, implantable medical device 1302 may include control logic that controls application of the therapy. For example, logic unit 1350 may control parameters of the therapy such as timing, duty cycle, current amplitude, voltage amplitude, and frequency of signals applied to the target tissue.

Communication unit 1360 may communicate with monitoring device 102, base station 1108, and/or one or more computing devices 1112. Controller 1310 may be utilized to control one or more elements of implantable medical device 1302. One or more processors 1315 may execute program instructions of memory 1317 and use memory 1317 for data storage. One or more processors 1315 may also include a numeric co-processor, or a graphics processing unit (or units) for accelerated video encoding and decoding, and/or any combination thereof. One or more processors 1315 may include communication interfaces for communicating with various internal elements and/or external devices.

Memory 1317 may be non-volatile semiconductor memory, such as read-only memory ("ROM"), erasable programmable read-only memory ("EPROM"), electrically erasable programmable read-only memory ("EEPROM"), flash memory ("NVRAM"), Nano-RAM (e.g., carbon nanotube random access memory), and/or any combination thereof. Memory 1317 may also be volatile semiconductor memory such as, dynamic random access memory ("DRAM"), static random access memory ("SRAM"), and/or any combination thereof. Memory 1317 may be used to store read-only program instructions for execution by one or more processors 1315, for the read-write storage for global variables and static variables, read-write storage for uninitialized data, read-write storage for dynamically allocated memory, for the read-write storage of the data structure known as "the stack," and/or any combination thereof.

Power supply 1330 may be any type of power supply to power implantable medical device 1302. Magnetic field detection unit 1390 may detect one or more magnetic fields to protection and/or power implantable medical device 1302. Seizure detection module 1340 may detect, compile, store, implement, and/or transmit data relating to one or more seizure detections. This seizure detection module 1340 may be in any device (e.g., implantable medical device 1302, monitoring device 102, base station 1108, one or more computing devices 1112, etc.) and communicate with another other device (e.g., implantable medical device 1302, monitoring device 102, base station 1108, one or more computing devices 1112, etc.). External unit 1370 may be an external programming unit, an external monitoring device, an external control unit, an external computing unit, an external communication unit, and/or any other unit external (e.g., monitoring device 102, base station 1108, one or more computing devices 1112, etc.) to implantable medical device 1302.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

As used herein, the term "mobile device" refers to a device that may from time to time have a position that changes. Such changes in position may comprise of changes to direction, distance, and/or orientation. In particular examples, a mobile device may comprise of a cellular telephone, wireless communication device, user equipment, laptop computer, other personal communication system ("PCS") device, personal digital assistant ("PDA"), personal audio device ("PAD"), portable navigational device, or other portable communication device. A mobile device may also comprise of a processor or computing platform adapted to perform functions controlled by machine-readable instructions.

The methods and/or methodologies described herein may be implemented by various means depending upon applications according to particular examples. For example, such methodologies may be implemented in hardware, firmware, software, or combinations thereof. In a hardware implementation, for example, a processing unit may be implemented within one or more application specific integrated circuits ("ASICs"), digital signal processors ("DSPs"), digital signal processing devices ("DSPDs"), programmable logic devices ("PLDs"), field programmable gate arrays ("FPGAs"), processors, controllers, micro-controllers, microprocessors, electronic devices, other devices units designed to perform the functions described herein, or combinations thereof.

Some portions of the detailed description included herein are presented in terms of algorithms or symbolic representations of operations on binary digital signals stored within a memory of a specific apparatus or a special purpose computing device or platform. In the context of this particular specification, the term specific apparatus or the like includes a general purpose computer once it is programmed to perform particular operations pursuant to instructions from program software. Algorithmic descriptions or symbolic representations are examples of techniques used by those of ordinary skill in the arts to convey the substance of their work to others skilled in the art. An algorithm is considered to be a self-consistent sequence of operations or similar signal processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals, or the like. It should be understood, however, that all of these or similar terms are to be associated with appropriate physical quantities and are merely convenient labels. Unless specifically stated otherwise, as apparent from the discussion herein, it is appreciated that throughout this specification discussions utilizing terms such as "processing," "computing," "calculating," "determining" or the like refer to actions or processes of a specific apparatus, such as a special purpose computer or a similar special purpose electronic computing device. In the context of this specification, therefore, a special purpose computer or a similar special purpose electronic computing device is capable of manipulating or transforming signals, typically represented as physical electronic or magnetic quantities within memories, registers, or other information storage devices, transmission devices, or display devices of the special purpose computer or similar special purpose electronic computing device.

Reference throughout this specification to "one example," "an example," "embodiment," and/or "another example" should be considered to mean that the particular features, structures, or characteristics may be combined in one or more examples and/or in any example. For instance, Example 1 shows element X and Example 2 shows element Y. Therefore, Element X and Element Y may be used together in one embodiment.

What is claimed is:

1. An external monitoring device located on a patient comprising:
   one or more processors;
   one or more memory devices;
   one or more power devices;
   one or more heart rate detection devices configured to determine heart rate data;
   one or more heart sound detection devices configured to determine sound data; and
   a validation module, the validation module configured to determine a heart rate status based on the determined heart rate data and a heart sound status based on the determined sound data, the validation module configured to determine an external monitoring device condition based on both the heart rate status and the heart sound status.

2. The external monitoring device of claim 1, wherein at least one of the one or more heart sound detection devices is an accelerometer.

3. The external monitoring device of claim 1, wherein the one or more processors are configured to determine via the validation module a first external monitoring device condition, the first external monitoring device condition being that the external monitoring device has not been placed on the patient.

4. The external monitoring device of claim 1, wherein the one or more processors are configured to determine via the validation module a second external monitoring condition, the second external monitoring condition being that the external monitoring device is misaligned on the patient.

5. The external monitoring device of claim 1, wherein the one or more processors are configured to determine via the validation module a third external monitoring condition, the third external monitoring condition being that an error has occurred on at least one of a patch and an electrocardiography signal generator.

6. The external monitoring device of claim 1, wherein the one or more processors are configured to determine via the validation module a fourth external monitoring condition, the fourth external monitoring condition being that the external monitoring device is located in a tolerance range.

7. A method for determining a status of an external monitoring device located on a patient comprising:
obtaining via one or more processors heart rate data;
obtaining via the one or more processors heart sound data;
determining via the one or more processors a heart rate status based on the heart rate data and a heart sound status based on the heart sound data; and
determining via the one or more processors an external monitoring device state utilizing a validation module, the validation module being configured to determine an external monitoring device condition based on both the heart rate status and the heart sound status.

8. The method of claim 7, further comprising determining a location of the external monitoring device; and
modifying the validation module based on the determined external monitoring device location.

9. The method of claim 8, further comprising determining the external monitoring device state via an adjusted validation module based on the heart rate status and the heart sound status.

10. The method of claim 7, further comprising determining a first external monitoring device condition, the first external monitoring device condition being that the external monitoring device has not been placed on the patient.

11. The method of claim 7, further comprising a second external monitoring condition, the second external monitoring condition being that the external monitoring device is misaligned on the patient.

12. The method of claim 7, further comprising a third external monitoring condition, the third external monitoring condition being that an error has occurred on at least one of a patch and an electrocardiography signal generator.

13. The method of claim 7, further comprising a fourth external monitoring condition, the fourth external monitoring condition being that the external monitoring device is located in a tolerance range.

14. A system comprising:
an external monitoring device located on a patient including one or more processors, one or more memory devices, one or more power devices, one or more heart rate detection devices configured to determine heart rate data, and one or more heart sound detection devices configured to determine sound data, the external monitoring device further comprises a validation module, the validation module configured to determine a heart rate status based on the determined heart rate data and a heart sound status based on the determined sound data, the validation module configured to determine an external monitoring device condition based on both the heart rate status and the heart sound status;
a base station including a base station processor, a base station memory, and a base station power supply; and
an external device including an external device processor, an external device memory, and an external device power supply.

15. The system of claim 14, wherein at least one of the one or more heart sound detection devices is an accelerometer.

16. The system of claim 14, wherein the one or more processors are configured to determine via the validation module a first external monitoring device condition, the first external monitoring device condition being that the external monitoring device has not been placed on the patient.

17. The system of claim 14, wherein the one or more processors are configured to determine via the validation module a second external monitoring condition, the second external monitoring condition being that the external monitoring device is misaligned on the patient.

18. The system of claim 14, wherein the one or more processors are configured to determine via the validation module a third external monitoring condition, the third external monitoring condition being that an error has occurred on at least one of a patch and an electrocardiography signal generator.

19. The system of claim 14, wherein the one or more processors are configured to determine via the validation module a fourth external monitoring condition, the fourth external monitoring condition being that the external monitoring device is located in a tolerance range.

20. An implantable medical system comprising:
an implantable medical device; and
an external monitoring device including one or more processors, one or more memory devices,
one or more power devices, one or more heart rate detection devices configured to determine heart rate data, one or more heart sound detection devices configured to determine heart sound data, a validation module configured to determine a heart rate status based on the determined heart rate data and an heart sound status based on the determined heart sound data, the validation module configured to determine an external monitoring device condition based on both the heart rate status and the heart sound status.

21. The implantable medical system of claim 20, wherein at least one of the one or more heart sound detection devices is an accelerometer.

22. The implantable medical system of claim 20, wherein the external monitoring device is configured to determine an implantable medical device orientation based on at least one of the plurality of conditions.

23. The implantable medical system of claim 22, wherein the external monitoring device is further configured to modify one or more antenna characteristics based on one or more of the plurality of conditions.

* * * * *